(12) United States Patent
Batenburg et al.

(10) Patent No.: US 9,619,902 B2
(45) Date of Patent: Apr. 11, 2017

(54) FILTER FOR TOMOGRAPHIC RECONSTRUCTIONS

(75) Inventors: Kees Joost Batenburg, Oegstgeest (NL); Jan Sijbers, Duffel (BE); Linda Plantagie, Zeist (NL)

(73) Assignees: Universiteit Antwerpen, Antwerp (BE); CWI, Amsterdam (NL)

( * ) Notice: Subject to any disclaimer, the term of this patent is extended or adjusted under 35 U.S.C. 154(b) by 363 days.

(21) Appl. No.: 14/233,585

(22) PCT Filed: Jul. 17, 2012

(86) PCT No.: PCT/EP2012/064016
§ 371 (c)(1),
(2), (4) Date: Feb. 25, 2014

(87) PCT Pub. No.: WO2013/011031
PCT Pub. Date: Jan. 24, 2013

(65) Prior Publication Data
US 2014/0219417 A1    Aug. 7, 2014

(30) Foreign Application Priority Data

Jul. 19, 2011  (GB) .................................. 1112359.3

(51) Int. Cl.
*G06K 9/00* (2006.01)
*G06T 11/00* (2006.01)
*G01N 23/04* (2006.01)

(52) U.S. Cl.
CPC .......... *G06T 11/003* (2013.01); *G01N 23/046* (2013.01); *G06T 11/006* (2013.01);
(Continued)

(58) Field of Classification Search
USPC ................................................ 382/128–134
See application file for complete search history.

(56) References Cited

U.S. PATENT DOCUMENTS 5,588,032 A    12/1996 Johnson et al.
5,848,114 A    12/1998 Kawai et al.
(Continued)

FOREIGN PATENT DOCUMENTS

JP        10146334 A       6/1998
WO    2004087060 A2      10/2004

OTHER PUBLICATIONS

GB Search Report for corresponding GB Application No. 1112359.3, mailed Nov. 11, 2011.
(Continued)

*Primary Examiner* — Alex Liew
(74) *Attorney, Agent, or Firm* — Workman Nydegger

(57) ABSTRACT

A method for applying a filter component for an analytical tomographic reconstruction technique, e.g. filtered backprojection, used in tomographic comprises providing an algebraic reconstruction algorithm for reconstructing a spatial representation of a volume of interest from a projection data set. It thereby takes into account a geometry of the tomographic imaging. The method also comprises applying the algebraic reconstruction algorithm to a plurality of virtual projection data sets—corresponding with a basis vector of a basis for the projection space—to produce a plurality of reconstructed spatial representations and determining the filter component using the plurality of reconstructed spatial representations, and applying the filter. Applying the analytical reconstruction technique with the determined filter component may inherit beneficial properties from the algebraic reconstruction algorithm, e.g. versatility and robustness to noise, without incurring the associated computational cost.

19 Claims, 27 Drawing Sheets

(52) U.S. Cl.
CPC ... *G06T 2211/421* (2013.01); *G06T 2211/424* (2013.01); *G06T 2211/436* (2013.01)

(56) References Cited

U.S. PATENT DOCUMENTS

| | | |
|---|---|---|
| 7,015,477 B2 | 3/2006 | Gunter |
| 7,447,295 B2 | 11/2008 | Hoheisel et al. |
| 2003/0161443 A1 | 8/2003 | Xiao et al. |
| 2004/0251418 A1 | 12/2004 | Gunter |
| 2007/0093711 A1 | 4/2007 | Hoheisel et al. |
| 2008/0247502 A1* | 10/2008 | Liao ............... G01N 23/046 378/4 |
| 2009/0123048 A1 | 5/2009 | Leroux et al. |
| 2010/0284599 A1 | 11/2010 | Fujita et al. |
| 2011/0135182 A1 | 6/2011 | Goto et al. |

OTHER PUBLICATIONS

International Search Report for corresponding International PCT Application No. PCT/EP2012/064016, mailed Oct. 16, 2012.

\* cited by examiner

FILTER FOR TOMOGRAPHIC RECONSTRUCTIONS

FIELD OF THE INVENTION

The invention relates to the field of tomographic imaging. More specifically it relates to methods and systems for reconstruction of a spatial representation of an object from projection data and products assisting therein.

BACKGROUND OF THE INVENTION

In tomographic imaging, penetrating waves are used to gather projection data from an object under study from multiple directions. Different tomographic imaging modalities exist for different types of penetrating waves, for example, computed tomography generally refers to X-ray tomography, single-photon emission computed tomography and positron emission tomography refer to gamma ray tomography, magnetic resonance imaging uses radiofrequent waves, and other modalities exist for visible light, electron waves and ultrasound.

In the case of computed tomography, internal structure of a patient or object may be examined non-invasively. This typically involves the collection of projection data using a detector which performs measurements relating to x-ray beams cast through the patient or object from various angles by a moving x-ray source. This allows to calculate the distribution of beam attenuation properties inside the patient or object, for example in the single plane of rotation of the moving x-ray source, or even such a distribution in a 3D volume, for example by combining a source rotating in a plane with a translation of the object of patient in a direction perpendicular to this plane.

The reconstruction of a spatial representation, e.g. a planar image or a 3D image volume, from such projection data, may be achieved by using algorithms known in the art. Most reconstruction algorithms can be subdivided in two classes: analytical reconstruction techniques, e.g. variants of filtered backprojection (FBP), and iterative algebraic methods, such as Algebraic Reconstruction Technique (ART), Simultaneous Algebraic Reconstruction Technique (SART) or Simultaneous Iterative Reconstruction Technique (SIRT). Furthermore, hybrid reconstruction methods are known in the art. Such methods may combine both types of reconstruction algorithms, for example by using an FBP reconstruction as the initial solution for an algebraic method.

Filtered backprojection is a high-performance analytical reconstruction technique, and yields accurate results when a large number of projections are available, data is acquired with a high signal-to-noise ratio (SNR) and a full 180° angular range is covered by the projections. This technique is characterized by the two operations, filtering and backprojection, e.g. performing a discrete inverse Radon transform. Backprojection involves the redistribution of projection data values over points along the corresponding projection lines in space, while filtering involves weighting the projection data to counteract blurring of the backprojected image. The applied filtering, for example as defined by a convolution kernel, therefore determines the image quality of an image reconstruction to a great extent. The ideal convolution kernel depends on the specific imaging methodology, and may only be determined analytically in idealized situations, e.g. neglecting discretization effects, projections obtained by rotation along a circular path involving a fixed angular step size and covering a full rotation.

Alternatively, tomographic reconstruction may be carried out using algebraic reconstruction algorithms, such as the well-known ART, SIRT or similar algorithms. These methods do not depend on filters, and therefore circumvent difficulties in determining suitable filters for filtered backprojection in complex imaging geometries. These algorithms may typically involve iteratively adjusting an image to minimize a difference metric between simulated projection data for this image and the measured projection data. Algebraic reconstruction methods may be considered more flexible in dealing with limited data problems and noise compared to filtered backprojection. They may furthermore allow for incorporation of certain types of prior knowledge, e.g. constraints such as non-negativity of the reconstructed image, by adjusting the image between subsequent iterations. Unfortunately, the iterative nature of these methods renders them computationally more intensive.

In the patent specification U.S. Pat. No. 7,447,295 B2, a method is disclosed for providing filters for use in filtered backprojection, which are specifically attuned to a predetermined scanning geometry. This method involves using an algebraic reconstruction algorithm, e.g. ART, in calculating a filter. Particularly, this method uses projection data obtained for a test object, e.g. a thin wire or other object with preferably a broad spatial frequency bandwidth, to calculate a filter for application in filtered backprojection. Alternatively to obtaining projection data by actually imaging a test object, this tomographic imaging may be simulated.

SUMMARY OF THE INVENTION

It is an object of embodiments of the present invention to provide efficient methods and systems for reconstructing spatial representations in tomographic imaging.

It is an advantage of embodiments according to the present invention that a filter may be provided that combines the favorable properties of an algebraic reconstruction technique, e.g. robustness to noise and able to handle limited projection data, with the computational efficiency of an analytical reconstruction technique, e.g. filtered backprojection.

It is an advantage of embodiments of the present invention that filters can be determined for any suitable configuration of the tomographic imaging system.

It is an advantage of embodiments of the present invention that filters can be provided for a particular algebraic reconstruction algorithm, without stringent limitation of the algebraic reconstruction algorithm.

It is an advantage of embodiments according to the present invention that filters can be determined which do not depend in any way on the scanned object. Consequently, although the computation time for determining a filter may be substantially larger than the computation time for a single algebraic reconstruction of an image, the filter can be re-used and as the computation time for reconstruction using the filter is significantly smaller than the computation time using a single algebraic reconstruction, embodiments of the present invention result in efficient methods for reconstruction, as the same filter can be used for reconstructing an arbitrarily large number of datasets.

It is an advantage of embodiments according to the present invention that if the geometrical parameters (projection angles, detector size and position) of the scanning device are fixed, the same filter can be used for reconstruction, which is advantageous as the majority of commercial CT scanners only have a few different acquisition schemes and after computing the filters for these schemes once, reconstruction can be calculated significantly quicker than e.g. using algebraic reconstruction algorithms.

The above objective is accomplished by a method and device according to the present invention.

In a first aspect, the present invention relates to a method for applying, in a tomographic imaging system, a filter component for an analytical tomographic reconstruction technique used in tomographic imaging. The method comprises obtaining an algebraic reconstruction algorithm for reconstructing a spatial representation of a volume of interest from a projection data set, the algebraic reconstruction algorithm taking into account a geometry of the tomographic imaging. The method further comprises applying the algebraic reconstruction algorithm to a plurality of virtual projection data sets to produce a plurality of reconstructed spatial representations, in which each virtual projection data set corresponds with a basis vector of a basis for the projection space. The method also comprises determining, e.g. calculating, the filter component using the plurality of reconstructed spatial representations. The method furthermore comprises implementing the filter component in the tomographic imaging system.

In another aspect, the present invention relates to a method for calculating a filter component, also referred to as filter, for an analytical tomographic reconstruction technique used in tomographic imaging. The method comprises obtaining an algebraic reconstruction algorithm for reconstructing a spatial representation of a volume of interest from a projection data set, the algebraic reconstruction algorithm taking into account a geometry of the tomographic imaging. The method further comprises applying the algebraic reconstruction algorithm to a plurality of virtual projection data sets to produce a plurality of reconstructed spatial representations, in which each virtual projection data set corresponds with a basis vector of a basis for the projection space. The method also comprises calculating the filter component using the plurality of reconstructed spatial representations.

The virtual projection data set may correspond with a basis vector comprising exactly one non-zero element, e.g. a vector $[0,0, \ldots, 0,1,0, \ldots, 0]$. Provision of such a virtual projection data set may result in calculation of one column of the matrix representing the set of filters used for different detection elements and for different projection angles.

The algebraic method used to compute the filter may be a linear algebraic method.

Determining of the filter component may comprise combining values from the plurality of reconstructed spatial representations corresponding to at least one reference location in the space of the spatial representation of the volume of interest. It is an advantage of embodiments according to the present invention that a filter component that provides an exact reconstruction for at least one point in space can be provided.

The plurality of virtual projection data sets may comprise at least two non-zero elements corresponding to different projection angles according to said geometrical characterization, so that calculating comprises calculating a filter component having dedicated components for each of the different projection angles. It is an advantage of embodiments according to the present invention that a more accurate reconstruction can be obtained and/or a reduction of artefacts can be obtained, by weighing both as function of detector element and as function of detection angle. It is an advantage that an accurate reconstruction similar to algebraic reconstruction methods can be obtained while having the computational benefit of a filtered back projection method. It is an advantage of embodiments according to the present invention that methods and systems are provided that allow reconstruction of limited angle acquisitions. It is an advantage of embodiments according to the present invention that methods and systems are provided that allow reconstruction of data obtained at irregular angular intervals, allowing irregular sampling which may be advantageous for certain applications.

The at least one reference location may comprise the geometrical center of the volume of interest. It is an advantage of embodiments according to the present invention that relatively easy computing of the filter components can be performed. It is an advantage of embodiments according to the present invention that filter components for reconstructing the entire field of view can be obtained while using a single reference location.

Said taking into account a geometry of the tomographic imaging may comprise characterizing the geometry with a projection matrix. Said taking into account a geometry of the tomographic imaging may comprise providing an algorithm for computing at least one element of a projection matrix, in which the projection matrix characterizes the geometry.

The determined filter component, when used in said analytical tomographic reconstruction technique to reconstruct a first spatial representation of a volume of interest from a projection data set obtained by performing said tomographic imaging, may produce a first value in the first spatial representation at said at least one reference location that is substantially equal to a second value in a second spatial representation at said at least one reference location, in which the second spatial representation is obtained by applying said algebraic reconstruction algorithm to the projection data set. It is an advantage of embodiments that for at least one point an exact reconstruction is obtained using the filter component as would be obtained using the selected tomographic reconstruction technique.

The algebraic reconstruction algorithm may comprise ART or SIRT.

The analytic tomographic reconstruction technique may comprise filtered backprojection.

In a second aspect, the present invention relates to an analytic tomographic reconstruction method for reconstructing a spatial representation of a volume of interest. This method comprises the steps of providing a filter component calculated using a method according to the first aspect of the present invention, determining projection data by scanning the volume of interest with a tomographic imaging device, the projection data comprising a plurality of projection views obtained from a plurality of projection angles, each projection view comprising a plurality of observation values obtained at a plurality of detection locations, and reconstructing the spatial representation of the volume of interest using the projection data, the filter and a backprojection operation. At least one sectional planar representation of the volume of interest may be reconstructed. At least one volumetric representation of the volume of interest may be reconstructed.

The projection data may be determined using conical beam geometry. The projection data may be determined using fan beam geometry.

Reconstructing may comprise applying the filter component resulting in a least square approximation resulting in an effective averaging of noise on the projection data.

In a third aspect, the present invention relates to a system for performing tomographic reconstruction, the system comprising an input means for inputting projection data produced by executing a tomographic imaging protocol for scanning a volume of interest, a storage means for storing a filter component suitable for an analytical tomographic reconstruction technique and said tomographic imaging protocol, said filter component being calculated using a method according to the first aspect of the present invention, a processing means programmed for performing said analytical reconstruction technique and thus reconstructing a spatial representation of the volume of interest taking into account the projection data and the filter component, and an output means for outputting the spatial representation of the volume of interest.

The present invention also relates to a filter component for an analytical tomographic reconstruction technique used in tomographic imaging, obtained by a method according to the first aspect of the present invention. The present invention relates furthermore to a computer program product for, when executing on a processing means, carrying out a method according to the present invention. The present invention relates further to a data storage device or a data carrier for storing a filter component according to the present invention. The present invention relates furthermore to a data storage device or a data carrier for storing a computer program product according to the present invention. The present invention relates further to an image or volumetric image obtained by an analytic tomographic reconstruction method for reconstructing a spatial representation of a volume of interest according to the present invention.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

Figure 1:
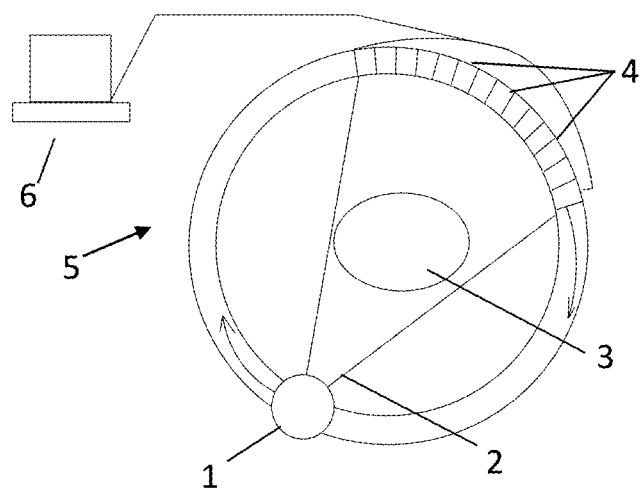
FIG. 1 illustrates a schematic overview of a tomographic imaging system that could be used in embodiments according to the present invention.

The drawings are only schematic and are non-limiting. In the drawings, the size of some of the elements may be exaggerated and not drawn on scale for illustrative purposes.

Any reference signs in the claims shall not be construed as limiting the scope. In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Embodiments of the present invention relate to filters that are especially suitable for use in or with a tomographic imaging system or are part of such a tomographic imaging system.

Such tomographic imaging system may for example be a computed tomography (CT) imaging or tomosynthesis imaging system, for example such systems as used in medical or veterinary examination, non-destructive testing or sample analysis. By way of illustration, embodiments of the present invention not being limited thereto, a tomographic imaging system suitable for using a filter component, also referred to as filter, according to an embodiment of the present invention or comprising such a filter component will now first be described with reference to FIG. 1, for illustrating the larger system in which a filter component according to embodiments of the present invention is used. The filter component typically may be implemented as a computational filter component in a computing device of the tomographic imaging system. FIG. 1 schematically illustrates such a system 5 for tomographic imaging, also comprising a number of components conventionally present in a tomographic imaging system.

The system for example typically may comprise a radiation source 1, e.g. an x-ray source. Such x-ray source may for example comprise a vacuum tube having a tungsten anode connected to a high-voltage power supply, e.g. supplying an adjustable voltage, such as in one example a voltage up to 200 kV, or such x-ray source may for example comprise a linear accelerator for producing x-ray beams in the megavolt range. Alternatively, the radiation source 1 may comprise an electron gun for producing an electron beam, an UV, visible or IR light source, an antenna for emitting radiofrequent radiation, a gamma radiation source, a neutron radiation source or an ultrasound emitter.

This radiation source may be arranged so as to project radiation 2, e.g. an x-ray beam, gamma radiation, neutron radiation, an ultrasound wave, visible, UV or IR light or radiofrequent radiation, through a volume of interest, e.g. a volume containing a test object 3, for example a body part of a patient under study, a weld, an archeological artifact or a microscopy sample. The spectral properties of the radiation beam 2 may furthermore be conditioned by means of fixed or removable filters, e.g. metallic absorbers, for example comprising lead, tungsten and/or cupper absorbers, for removing or reducing undesirable wavelengths from the beam 2. The beam may also be collimated and/or focused by one or more lenses and/or collimator elements as appropriate for the volume of interest. An object placed in the volume of interest, e.g. test object 3, may be supported by a suitable holding means, e.g. a sample holder or patient table, which may be constructed of material which is sufficiently radiolucent for radiation emitted by the radiation source. Such system 5 further typically may comprise a detector, such as an array of detector elements 4 in which each element measures a quantity indicative of the intensity of the radiation passing through the volume of interest, e.g. through the test object 3, along a well-defined line connecting the radiation source and this detector element 4. The radiation source 1 of such a tomographic imaging system is adapted for projecting beams through the test object along different directions, such that the detector may obtain different projection views, i.e. data obtained by measuring quantities related to beams projecting through the test object under different angles. For example, the system 5 may have an x-ray source and an arc-shaped detector array rotating around a test object to record numerous projections, as shown in FIG. 1. Power supply to the x-ray source 1 and detector may be provided by means of a slip-ring gantry, e.g. by providing a sliding electrical contact when detector and x-ray source are rotating. The system 5 may have as little as one detector element 4, which may be used to collect data in a parallel beam geometry, i.e. by combining a scanning translation movement and a rotation movement of source and detector. A small number of detector elements may be used to speed up this translation and rotation scanning by collecting multiple data points simultaneously in an approximately parallel beam geometry. Advantageous configurations for CT scanners may use a large number of detector elements to obtain data over a large are simultaneously, thus only requiring a rotation movement of source and detector. These systems use a fan-beam geometry, which requires additional processing of the obtained data for image reconstruction. State-of-the-art CT scanners may even use a full circle arc of detector elements 4, avoiding the need to rotate the detector entirely. A test object 3 placed in the volume of interest, for example a patient, may furthermore be translated after each rotation cycle to obtain data over a range perpendicular to the rotation plane, i.e. to obtain a 3D image, e.g. a 3D image represented by a stack of 2D slices, e.g. reconstructed parallel cut plane images. Moreover, such object 3 may be moved in a continuous fashion while performing tomographic imaging, for example using a suitable holding means, such as a computer-controlled automated translation table. In this way a helical scan pattern may be obtained. The detector may even comprise multiple rows of detector elements, forming a two-dimensional detector array, to obtain data from several slices simultaneously or to allow helical scanning with a larger object translation speed as function of gantry rotation speed, thereby allowing a faster 3D image acquisition.

In certain applications, data acquisition may be limited to an angle of less than 180°. For example, in interventional radiology, CT imaging of a patient may be performed while medical personnel is positioned in close proximity to the patient, e.g. for performing a surgical intervention. In such cases, it is common practice to limit the arc wherein the radiation source is emitting to a vertically upward oriented cone, so as to shield medical personnel from backscattered radiation.

Thus, in a system 5 for tomographic imaging, the detector may be a single detector element 4, a one-dimensional array of elements or, as commonly found in such systems, a two-dimensional array of elements. The detector may be arc-shaped, as shown in FIG. 1, i.e. such that all elements of at least a single row of the detector are positioned substantially equidistant to the radiation source, or may be substantially flat. In some systems for tomographic imaging, e.g. in tomosynthesis systems used in mammography, the radiation source may rotate over a limited angle while a detector, e.g. a high resolution flat-panel direct radiography detector, translates along a single direction, thus collecting oblique projection views. Specific systems for tomographic imaging may move the radiation source over a non-circular arc.

The data obtained by a system 5 for tomographic imaging is then processed by a processing device or processor 6, e.g. a dedicated processing device programmed for calculating values indicative of beam attenuation properties of the matter contained in subvolumes of the test object. These values may then be used to form an image, e.g. a 2D image or 3D image volume, depicting variations in material properties within the test object 3, thus to obtain a reconstruction image representing this object. The processing device 6 may form an integrated part of the system 5 for tomographic imaging, or may be part of a separate computing system, e.g. only interacting with the system 5 for tomographic imaging by receiving data. Typically the filter component according to embodiments of the present invention will be embedded as a computational filter in the processing device 6. This data, e.g. projection data provided by the detector, may be transmitted over a transmission line, using wireless communications or by means of a physical data storage device or a data carrier, e.g. a magnetic or optical disc. The processing device 6 may furthermore be programmed for controlling the system 5, e.g. by driving the rotation of radiation source 1 and/or detector 4, the translation of a test object 3 in the volume of interest and determining beam properties, e.g. peak keV, filtration and intensity. Executing such tomographic imaging protocol, i.e. applying control parameters and actuating components in a coordinated, e.g. a timed, manner allows carrying out a specific tomographic imaging using the system 5. A system 5, e.g. a system for tomographic imaging controlled by a processing device 6, may typically be used to execute diverse tomographic imaging protocols, e.g. diverse tomographic imaging protocols optimized for specific types of test objects placed in the volume of interest or for obtaining specific information from a reconstructed spatial representation of the volume of interest.

Embodiments of the present invention relate to methods and systems for tomographic imaging, for example CT imaging or tomosynthesis as well as to products assisting therein. However, tomographic imaging in the sense of the present invention is not limited to X-ray tomographic imaging in the 10 keV to 400 keV range, but may equally apply to mega-volt applications, such as image reconstruction in radiotherapy, e.g. by processing of portal images or of measurements in tomotherapy. Furthermore, the present invention may also apply to optical imaging, e.g. optical CT, imaging with radiofrequency radiation, e.g. magnetic resonance, applications of emissive imaging, e.g. single photon emission computed tomography, or positron emission tomography, acoustic tomography, electron tomography or neutron tomography. While some of these tomographic imaging techniques require additional considerations in the processing and preparation of projection data before image reconstruction, as well as additional considerations in the operating of the corresponding imaging devices, these additional considerations are known to the skilled person.

Figure 2:
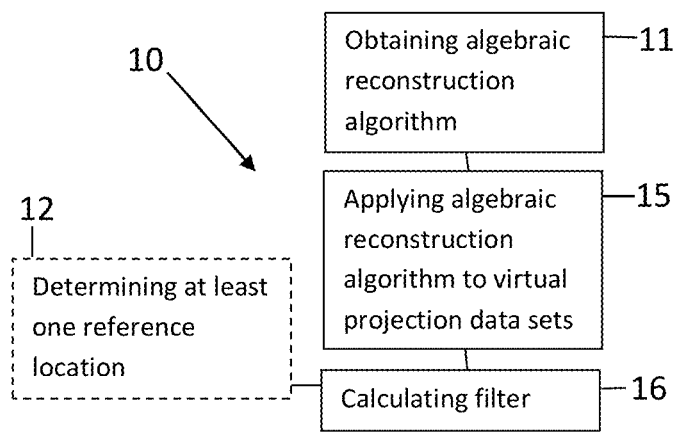
FIG. 2 illustrates a method for determining a filter component according to an embodiment of the present invention.

In a first aspect, the present invention relates to a method for applying a filter component for an analytical tomographic reconstruction technique used in tomographic imaging, for example but not limited to tomographic imaging as performed by operation of a tomographic imaging device as discussed hereabove in reference to FIG. 1. Alternatively the invention also relates to a method for calculating a filter for an analytical tomographic reconstruction technique used in tomographic imaging. An exemplary method 10 according to an embodiment of the first aspect of the present invention is discussed with reference to FIG. 2 by way of illustration, embodiments of the present invention not being limited thereto. Standard and optional features are discussed below with reference thereto.

According to the method, a filter component for an analytical tomographic reconstruction technique used in tomographic imaging is determined and implemented in a tomographic imaging device. Such tomographic imaging may for example be executed by means of a computed tomography scanner, a radiography device capable of performing tomosynthesis, a radiography device capable of performing cone-beam computed tomography, a portal imaging device for megavoltage tomography or tomosynthesis or an optical tomography scanner. The analytic tomographic reconstruction technique may comprise a backprojection operation. For example, a well-known analytic tomographic reconstruction technique is filtered backprojection. As suggested by the name, this technique comprises filtering projection data and backprojecting the filtered data. The filtering may be performed by convolution of the projection data by a filter, which, as known to the skilled person, may be performed by summation of the appropriately weighted projection data, or equivalently, by performing a point-wise multiplication in a frequency domain decomposition of the projection data such as obtainable by Fourier transformation, e.g. by using a discrete Fourier transform. The backprojection then comprises transformation of the filtered data, from the projection data space, to a reconstruction, in a spatial representation space. Alternatively, the analytic tomographic reconstruction technique may comprise backprojected filtering, which comprises performing a backprojection operation on the projection data, followed by performing a filtering operation in the spatial representation space. The filter referred to further herein, refers to a filter for transforming projection data in the native domain, e.g. not to the definition of such filter in the Fourier domain. This filter may be used in a convolution operation to transform projection data to filtered projection data. However, this is merely a representation of such filter, and an equivalent representation may be obtained in, for example, the frequency domain, e.g. by applying a discrete Fourier transform, such as a fast Fourier transform. Alternatively, a spatial image domain representation of this filter, as opposed to a projection domain representation, may be obtained. It will be seen by the skilled person that a number of operations may be performed to transform the filter to other representations, and that the filter, suitable for usage in filtered backprojection, may therefore be made suitable by means of trivial transformations for alternative analytical tomographic reconstruction techniques.

The method 10 for applying a filter component according to the first aspect of the present invention comprises obtaining 11 an algebraic reconstruction algorithm for reconstructing a spatial representation of a volume of interest from a projection data set. This algebraic reconstruction algorithm takes into account a geometry of the tomographic imaging. This geometry may depend on specific parameters associated with a tomographic imaging device used for performing the tomographic imaging, such as gantry dimensions, detector dimensions and collimator characteristics. This geometry may furthermore depend on specific parameters associated with carrying out a particular imaging protocol with this tomographic imaging device, such as rotation and/or translation speeds, step sizes, positioning of components of the system as function of time, e.g. gantry, radiation source, detector, collimators or translation table for a test object to be placed in the volume of interest, detector sampling rates and/or desired reconstruction characteristics, e.g. reconstructed field of view and resolution.

Taking into account of a geometry may comprise providing a description of spatial positions of detection elements in relation to radiation source and volume of interest, such that a model of each projection data element as a result of radiation passing through the volume of interest along well-defined beams may be constructed. Providing a description of spatial positions may comprise characterizing the geometry with a projection matrix, for example by characterizing a projection matrix consisting of numerical values arranged in rows and columns such that each row corresponds to a projection data element and each column corresponds to a spatial location in the volume of interest, in which these numerical values represent a contribution of a small subvolume centered around a spatial location in the volume of interest to the attenuation of the intensity of a radiation beam recorded by a projection data element. Such projection matrix may also be known in the art as a system matrix.

Providing a description of spatial positions may also comprise providing an algorithm for computing at least one element of a projection matrix. For example, storing the projection matrix may require a large amount of memory, for example more than $10^9$ numerical values, so that providing a method for calculating at least one element of the projection matrix without storing the entire projection matrix may be advantageous. Further advantageous representations of the projection matrix, of elements of the projection matrix, and/or submatrices of the projection matrix, may be used, such as a sparse matrix representation, to reduce memory usage and enhance computing performance when implementing the method 10 in a computer program or dedicated electronic processor.

The algebraic reconstruction algorithm may be a linear algebraic reconstruction algorithm. Moreover, the algebraic reconstruction algorithm may be an iterative scheme for obtaining a spatial representation of the volume of interest, e.g. the algebraic reconstruction algorithm may comprise any suitable algorithm, such as for example ART or SIRT. For example, the algebraic reconstruction algorithm may comprise a SIRT-like algorithm which may be formulated as the execution of a predetermined number, K, of iterations, $k=0, \ldots, K-1$, of the recursive set of equations $u^{(k+1)}=(I_n-\omega CW^T RW)u^{(k)}+\omega CW^T Rp$, where $C=(c_{ij})\in \mathfrak{R}^{n\times n}$, with $c_{ij}=0$ for $i\neq j$ and $$c_{jj} = \alpha\left(\sum_{i=1}^{m} |W_{ij}|\right),$$

i.e. C is a square diagonal matrix of n by n real scalar values $c_{jj}$, with the diagonal elements determined by a predefined scalar weighting function $\alpha$ taking column-wise absolute value sums of the projection matrix W. Further, $R=(r_{ij})\in \mathfrak{R}^{m\times m}$, another diagonal square matrix of m by m values, with the diagonal elements determined by a second scalar weighting function $\beta$, $$r_{jj} = \beta\left(\sum_{i=1}^{m} |W_{ij}|\right).$$

$\omega$ is a relaxation parameter. Thus, a projection data set p, comprising m numerical values $p_i$, is used in such an algorithm to obtain a spatial representation of the volume of interest $u^{(k+1)}$, comprising n numerical values $u^{(k+1)}_j$, e.g. numerical values corresponding to pixels in a planar image or to voxels in a 3D spatial representation, using a projection matrix W and a spatial representation of the volume of interest from a previous iteration, $u^{(k)}$. The first iteration may for example be initialized by an empty spatial representation, i.e. $u^{(0)}_i=0, \forall i\in\{1,2, \ldots, n\}$.

The method according to the first aspect of present invention further comprises applying 15 the algebraic reconstruction algorithm to a plurality of virtual projection data sets to produce a plurality of reconstructed spatial representations. The virtual projection data sets thereby correspond with basis vectors of a basis for the projection space.

Such basis may for example be a substantially orthogonal base, i.e. a set of orthogonal basis vectors or a set of vectors that are nearly orthogonal, as will be discussed later. It will be understood by the skilled person that any basis for the projection space may be used, as this merely requires a transformation of basis of the projection data before applying the analytical reconstruction technique, e.g. filtered backprojection, with the filter calculated by a method according to the first aspect of the present invention. While other beneficial basis choices may exist, the invention will, for the sake of clarity, further be described in terms of an orthogonal basis, e.g. a Cartesian basis, the invention not being limited in any way thereto.

The virtual projection data sets may correspond with basis vectors such that each such virtual projection data set comprises exactly one non-zero element. For example, a virtual projection data set p may be constructed such that $p_s=1$ and $p_i=0$ for $i=1,\ldots,s-1,s+1,\ldots,m$, thus, the virtual projection data set p may be a basis vector of the Cartesian basis of the space of projection data. The algebraic reconstruction algorithm, e.g. the SIRT-like algorithm discussed above, may then operate on this virtual projection data set p to produce a spatial representation u. In general, the spatial representation u, when being calibrated to represent beam attenuation by positive values on a monotonic scale, may contain negative values, i.e. might not represent beam attenuation in a physical object in a meaningful way. The virtual projection data therefore typically may not represent a projection data set obtainable by performing the tomographic imaging protocol on a physical object and the spatial representation u may in general not be a spatial representation of a physical object, e.g. a physical object as might be placed in the volume of interest.

The filter component is then determined, e.g. calculated, 16 using the plurality of reconstructed spatial representation obtained by applying 15 the algebraic reconstruction algorithm to the plurality of virtual projection data sets. Calculation of such a filter may be performed using a separate computing system or a computing cluster.

The filter component further is implemented on a tomographic imaging system, resulting in a tomographic imaging system having improved, e.g. faster operation.

For example, embodiments of the present invention not being limited thereby, the SIRT algorithm may be implemented on a state of the art, high-performance graphical processing unit (GPU). Such an implementation may take around 50 milliseconds per iteration for a 2D image having a size of 1024×1024 pixels when using 512 projections of 1024 detector measurements in a parallel beam geometry. Computing the filter that corresponds with 20 iterations of the SIRT algorithm may then require a separate run of the SIRT algorithm for each of the 512 angles, and for each of the 1024 detector elements. Each of these runs may take 1 second, resulting in a total running time of around 6 days using a single GPU. As all runs of the SIRT algorithm can be carried out independently, distributing the computation over a plurality of GPUs, possibly integrated in different computing systems, will divide the total duration of the filter computation by the number of GPUs.

For example, the filter component may be calculated by applying 15 the algebraic reconstruction algorithm to virtual projection data sets corresponding to all or a selection of basis vectors. For example when using Cartesian basis vectors and assuming the spatial representation $u^{(s)}$ corresponds to the reconstruction of virtual projection data set $p^{(s)}$, in which $p_s^{(s)}=1$ and $p_i^{(s)}=0$ for $i=1,\ldots,s-1,s+1,\ldots,m$, a matrix S may be constructed such that $S_{\cdot,s}=u^{(s)}$, i.e. the columns of S are formed by collecting the spatial representations $u^{(s)}$ in ascending order of s.

Finally, the method 10 according to the first aspect of the present invention may further comprise determining 12 at least one reference location in the space of the spatial representation of the volume of interest. For example, exactly one reference location may be determined, and the filter component may be formed in reference to this location by selecting a row $S_{i,\cdot}$ of the matrix S, e.g. corresponding to a reference location defined by the i'th element in the spatial representation of the volume of interest.

The application of such filter component in an analytical reconstruction technique such as filtered backprojection may then be demonstrated by the convolution of the filter and the projection dataset, i.e.

$$u_j(x_j, y_j) = \sum_{\theta \in \Theta} \sum_{t \in T} p_{\theta,t} h^{(j)}(\theta, t - x_j\cos\theta - y_j\sin\theta).$$

The filter may be defined as filter function $h^{(i)}(\theta, t-x_i \cos\theta - y_i \cos\theta) = S_{i,k}$, where the projection data set element k corresponds to the observation under angle $\theta$ and in detector element position t. This filter function $h^{(i)}$, defined only in $(\theta, t_i)$, i.e. the points t as function of $\theta$ corresponding to the elements $S_{i,\cdot}$, may be extended to cover the entire domain $(\theta, t)$ by common extrapolation and/or interpolation techniques. Also, it may be noted that choosing a reference location ($i_0$) corresponding to the geometrical center of the volume of interest, e.g. the center of rotation, i.e. where $x_i=y_i=0$, may simplify earlier expression to $h^{(i_0)}(\theta,t)=S_{i_0,k}$.

The values corresponding to the at least one reference location in the plurality of reconstructed spatial representations are used to calculate the filter component. For example, if the at least one reference location corresponds to the b'th value of the spatial representations, $u_b$, a filter component may be constructed by collecting such values $u_{b,s}$ corresponding to virtual projection data constructed such that $p_s=1$ and $p_i=0$ for $i=1,\ldots,s-1,s+1,\ldots,m$, for a plurality of virtual projection data sets corresponding to different choices of s. The plurality of virtual projection data sets may comprise at least two non-zero elements corresponding to different projection angles according to said geometry, so as to calculate a filter component having dedicated components for each of the different projection angles. Thus, for example, different choices of s for different virtual projection data sets may correspond to beams projected through the volume of interest at different angles, and may be collected in a filter with different filter components corresponding to these different angles. Alternatively formulated the filter component is actually a set of filters having an angular dependency. Commonly used filters for analytical reconstruction techniques, e.g. ramp filters, have no angular dependency. The calculation of a filter with explicit angular dependency may improve reconstruction accuracy and reduce artifacts in spatial reconstructions. This furthermore allows complex filtering and weighting to compensate for limited angle acquisitions, i.e. acquisitions taken over a maximal angular difference of substantially less than 180°, e.g. less than 120°, or less than 90°. The present invention furthermore may allow reconstruction of data obtained at irregular angular intervals, for example corresponding to portal imaging in a complex radiotherapy procedure.

Particularly, the values $u_{b,s}$ may be collected for all values $s=1,\ldots,m$, to obtain a filter component for every projection data element, corresponding to acquisitions under all angles in the tomographic imaging geometry and by all detector elements.

When the set of projection angles is regularly distributed between 0° and 180°, the computed angle-dependent filter components may also be averaged to form an angle-independent filter component that can be used for all projection angles.

While this disclosure, for the sake of clarity, focuses on two-dimensional images in a parallel beam geometry setting, it will be clear that extension to three-dimensional reconstruction, e.g. helical imaging e.g. performed by a multirow CT device, is straightforward for the person skilled in the art. The same applies to other variations such as accommodation of cone-beam or fan-beam geometries. For example, a rebinning step, as commonly performed in such analytical reconstruction techniques, may be required to format the projection data in an appropriate manner.

Furthermore, while for the above illustrative method a matrix representation is given, embodiments of the present invention are not limited thereto, in other words they are not limited by the mathematical formalism used for explanation.

A filter component determined, e.g. calculated, according to the method disclosed herein may be used in the analytical tomographic reconstruction technique to reconstruct a first spatial representation from a projection data set obtained by performing the tomographic imaging, e.g. imaging the volume of interest, for example the volume of interest containing an object under study, with a tomographic imaging device. Furthermore, a second spatial representation may be obtained by applying the algebraic reconstruction algorithm to this projection data set. The value in the first spatial representation and the second spatial representation, both corresponding to the reference location as used to calculate 16 the filter in the method 10, may then be substantially equal, e.g. equal to within rounding errors. The method 10 provided herein therefore allows to use a fast analytical tomographic reconstruction technique, e.g. filtered backprojection, to produce a result that is equal to a result produced by an algebraic reconstruction algorithm in at least one point. Surprisingly, the values in the first spatial representation not corresponding to the reference location may show few imaging artefacts and good reproduction of the second spatial representation as well.

When compared to analytical tomographic reconstruction techniques, e.g. filtered backprojection, algebraic reconstruction algorithms, e.g. SIRT, have better noise handling properties as they compute a certain least-square solution with respect to the measured dataset. This property may be inherited by the filter component in the method 10, such that the reconstruction that results from applying this filter component has a high correspondence with the measured data, in the least square sense. In particular, if an experimental dataset is noisy, the least square approximation that results from using the filter component in the method 10 may result in effective averaging of the noise, thereby improving the quality of the reconstructed image substantially compared to standard filtered backprojection. More particularly, at least for a particular image location, it also handles noise identically to the iterative method at that location.

In one embodiment the projection dataset may be a set of substantially orthogonal basis vectors, whereby the basis vectors comprise one element significantly different from 0 and other elements that are zero or close thereto. By using non-zero elements in the basis vectors that are close to zero, an additional noise filtering effect may be introduced, thus allowing to obtain filter components that are more robust to noise.

Figure 3:
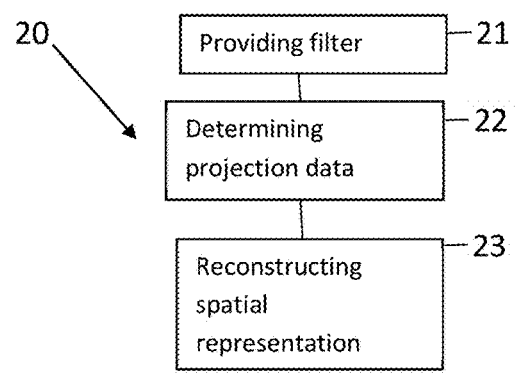
FIG. 3 illustrates a method for determining a reconstruction using a filter component according to an embodiment of the present invention.

In a second aspect, the present invention relates to an analytic tomographic reconstruction method for reconstructing a spatial representation of a volume of interest, e.g. the exemplary analytic tomographic reconstruction method 20 illustrated in FIG. 3. This reconstruction method comprises the step of providing a filter 21 calculated by a method according to the first aspect of the present invention.

A reconstruction method according to the second aspect of the present invention furthermore comprises determining 22 projection data by scanning the volume of interest with a tomographic imaging device, for example a device 5 as illustrated in FIG. 1. This projection data comprises a plurality of projection views obtained from a plurality of projection angles, each projection view comprising a plurality of observation values obtained at a plurality of detection locations. The projection data may for example be determined using conical beam geometry, or the projection data may be determined using fan beam geometry.

The reconstruction method 20 further comprises reconstructing 23 the spatial representation of the volume of interest using the projection data, the filter and a backprojection operation by applying the backprojection operation on the filtered projection data.

The spatial representation of the volume of interest may comprise at least one sectional planar representation, e.g. a 2D slice of an object. The spatial representation may also comprise a 3D volumetric representation of the volume of interest.

Figure 4:
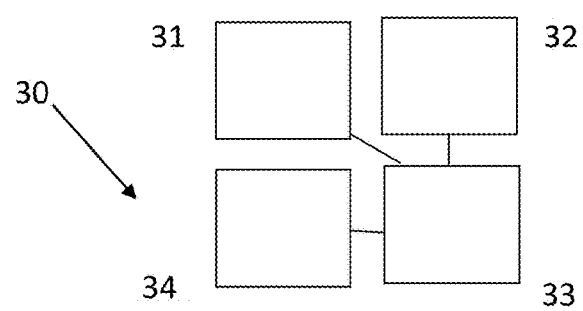
FIG. 4 illustrates a system for performing tomographic reconstruction according to an embodiment of the present invention.

In a third aspect, the present invention relates to a system 30 for performing tomographic reconstruction, such as the exemplary embodiment shown in FIG. 4. The system 30 comprises an input means 31 for inputting projection data produced by executing a tomographic imaging protocol for scanning a volume of interest.

The system 30 furthermore comprises a storage means 32 for storing a filter suitable for an analytical tomographic reconstruction technique and said tomographic imaging protocol, and calculated using a method according to the first aspect of the present invention.

The system 30 furthermore comprises a processing means 33 programmed for performing said analytical reconstruction technique and thus reconstructing a spatial representation of the volume of interest taking into account the projection data and the filter.

Finally, the system 30 comprises an output means 34 for outputting the spatial representation of the volume of interest.

In a fourth aspect, the present invention relates to a filter component for an analytical tomographic reconstruction technique used in tomographic imaging, obtained by a method according to the first aspect of the present invention.

In a fifth aspect, the present invention relates to a computer program product for, when executing on a processing means, for example in a device according to the third aspect of the invention, carrying out one of the methods according to the first or second aspect of the invention, as well as to a corresponding processing system. In other words, methods according to embodiments of the present invention may be implemented as computer-implemented methods, e.g. implemented in a software based manner One example of a processing system may be a processing system that includes at least one programmable processor coupled to a memory subsystem that includes at least one form of memory, e.g., RAM, ROM, and so forth. It is to be noted that the processor or processors may be a general purpose, or a special purpose processor, and may be for inclusion in a device, e.g., a chip that has other components that perform other functions. Thus, one or more aspects of embodiments of the present invention can be implemented in digital electronic circuitry, or in computer hardware, firmware, software, or in combinations of them. The processing system may include a storage subsystem that has at least one disk drive and/or CD-ROM drive and/or DVD drive. In some implementations, a display system, a keyboard, and a pointing device may be included as part of a user interface subsystem to provide for a user to manually input information. Ports for inputting and outputting data also may be included. More elements such as network connections, interfaces to various devices, and so forth, may be included. The various elements of the processing system may be coupled in various ways, including via a bus subsystem, in the present example for simplicity a single bus, but will be understood to those skilled in the art to include a system of at least one bus. The memory of the memory subsystem may at some time hold part or all of a set of instructions that when executed on the processing system implement the steps of the method embodiments described herein.

In further aspects, the present invention relates to a data storage device or a data carrier for storing a filter as described above or a data storage device or a data carrier storing a computer program product as described above or to the transmission of a computational filter or computer program product over a wide or local area network. Such a data storage device or a data carrier can thus tangibly embody a computer program product or filter as described above. The carrier medium therefore may carry machine-readable code for execution by a programmable processor. The present invention thus relates to a carrier medium carrying a computer program product that, when executed on computing means, provides instructions for executing any of the methods as described above or execute the filtering function of the filter described above. The term "carrier medium" refers to any medium that participates in providing instructions to a processor for execution. Such a medium may take many forms, including but not limited to, non-volatile media, and transmission media. Non volatile media includes, for example, optical or magnetic disks, such as a storage device which is part of mass storage. Common forms of computer readable media include, a CD-ROM, a DVD, a flexible disk or floppy disk, a tape, a memory chip or cartridge or any other medium from which a computer can read. Various forms of computer readable media may be involved in carrying one or more sequences of one or more instructions to a processor for execution. The computer program product can also be transmitted via a carrier wave in a network, such as a LAN, a WAN or the Internet. Transmission media can take the form of acoustic or light waves, such as those generated during radio wave and infrared data communications. Transmission media include coaxial cables, copper wire and fibre optics, including the wires that comprise a bus within a computer.

In still another aspect, the present invention relates to an image or volumetric image obtained by a method according to the second aspect of the invention.

Figure 5:
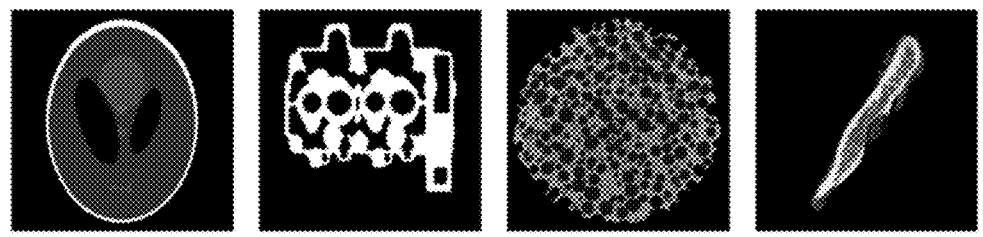
FIG. 5 illustrates four phantoms as used in exemplary experiments according to an embodiment of the present invention.
Figure 6A:
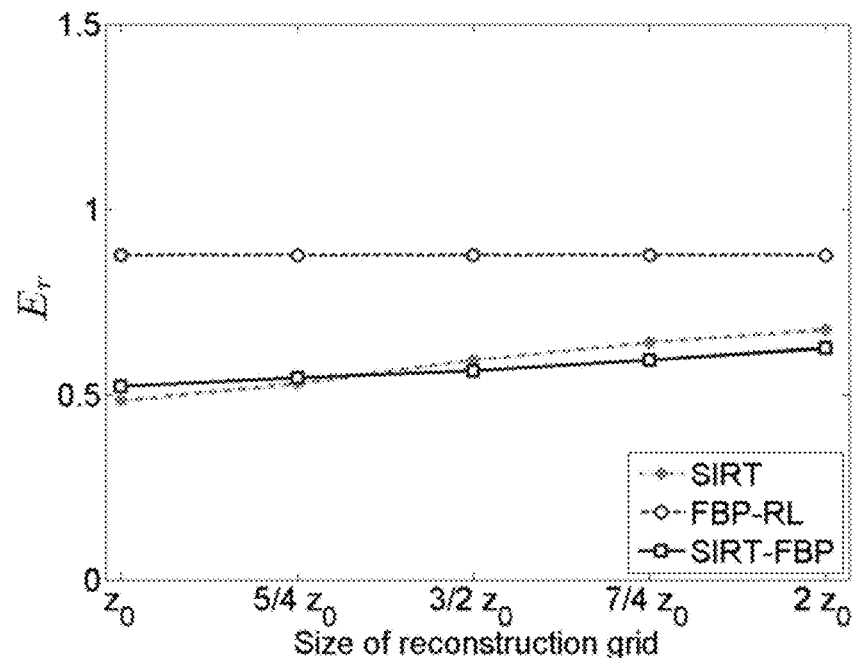
FIG. 6a to FIG. 6h and FIG. 7a to FIG. 7h show the reconstruction and projection errors as a function of the size of the reconstruction grid for different reconstruction methods, illustrating the advantages of embodiments of the present invention.
Figure 6B:
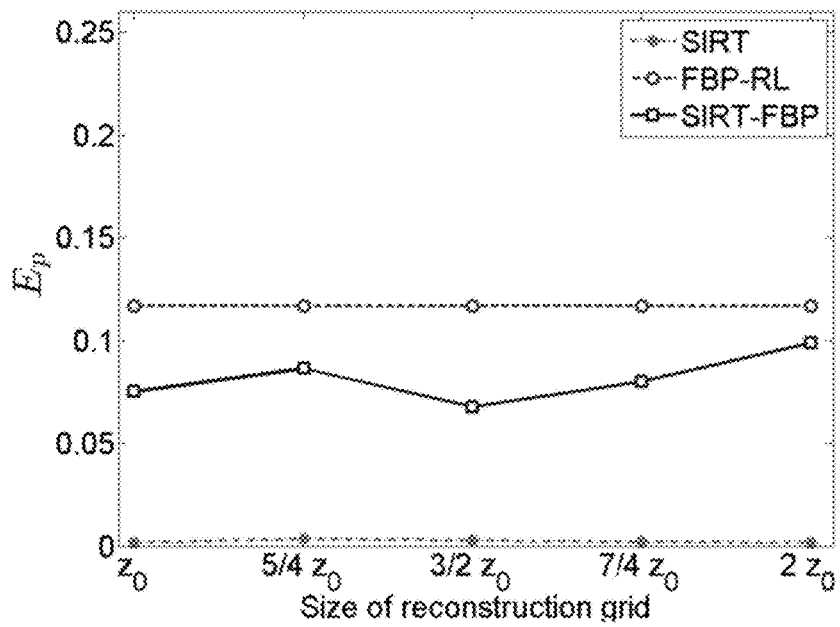
Figure 6C:
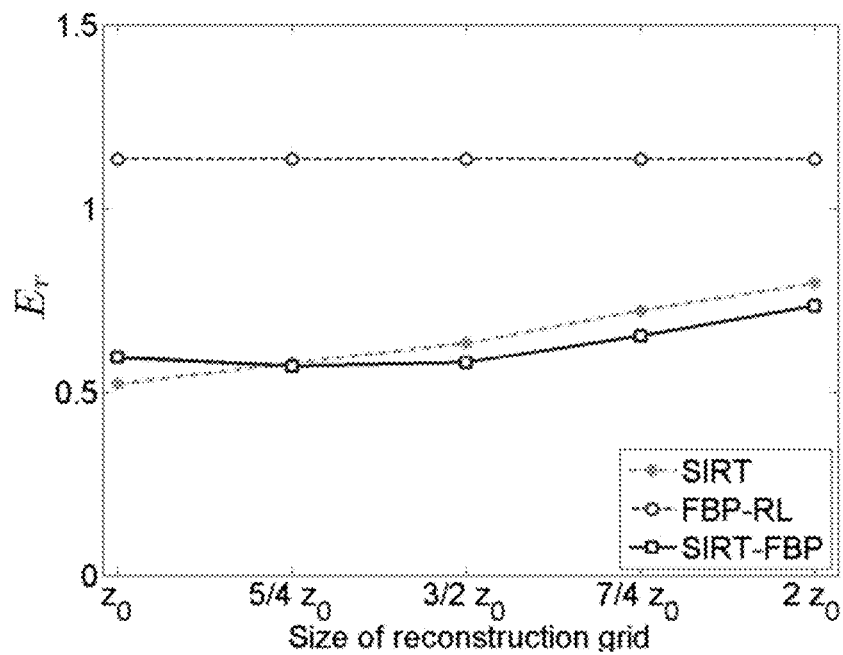
Figure 6D:
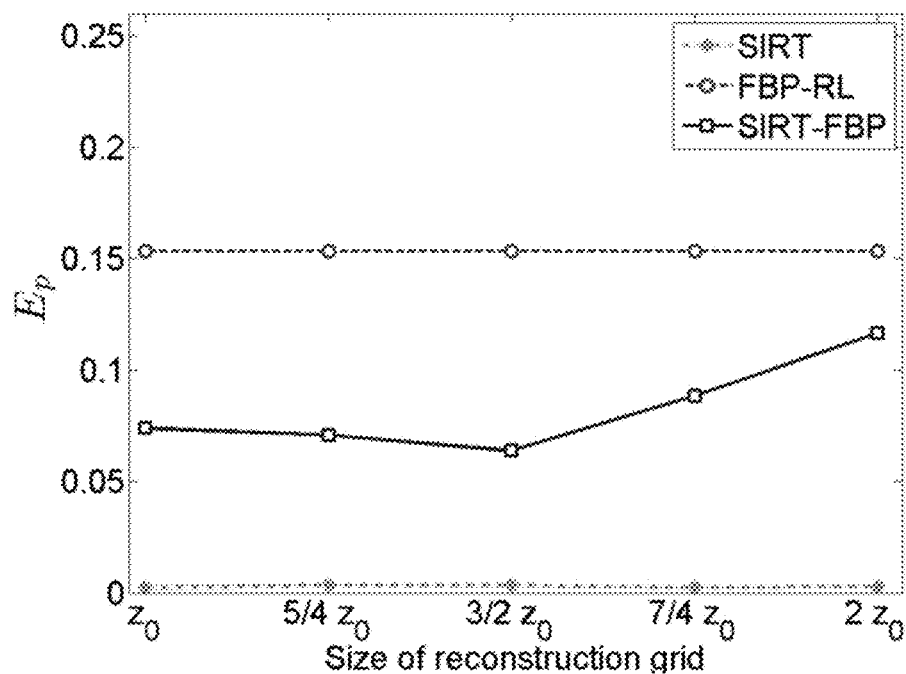
Figure 6E:
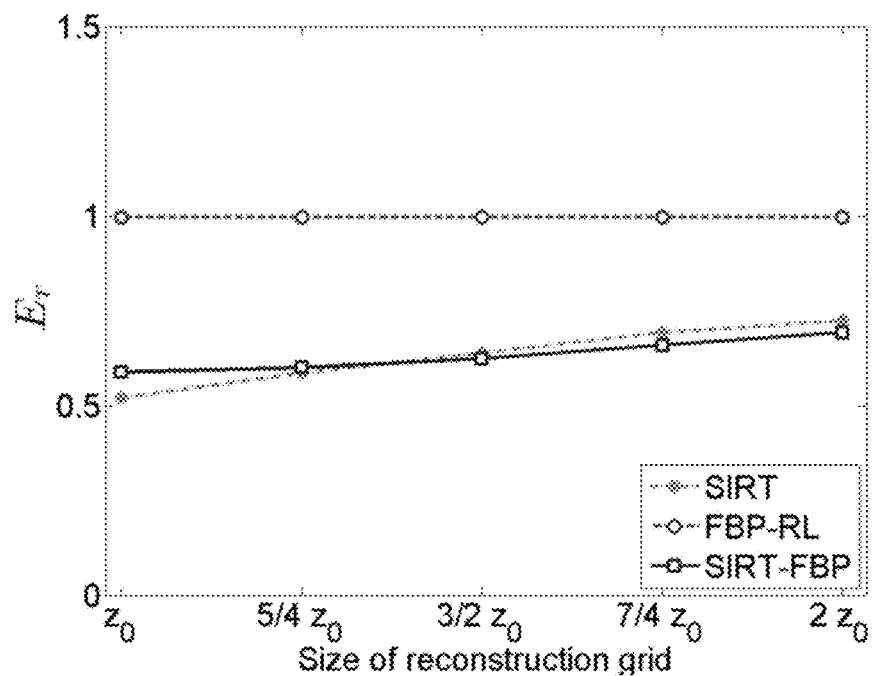
Figure 6F:
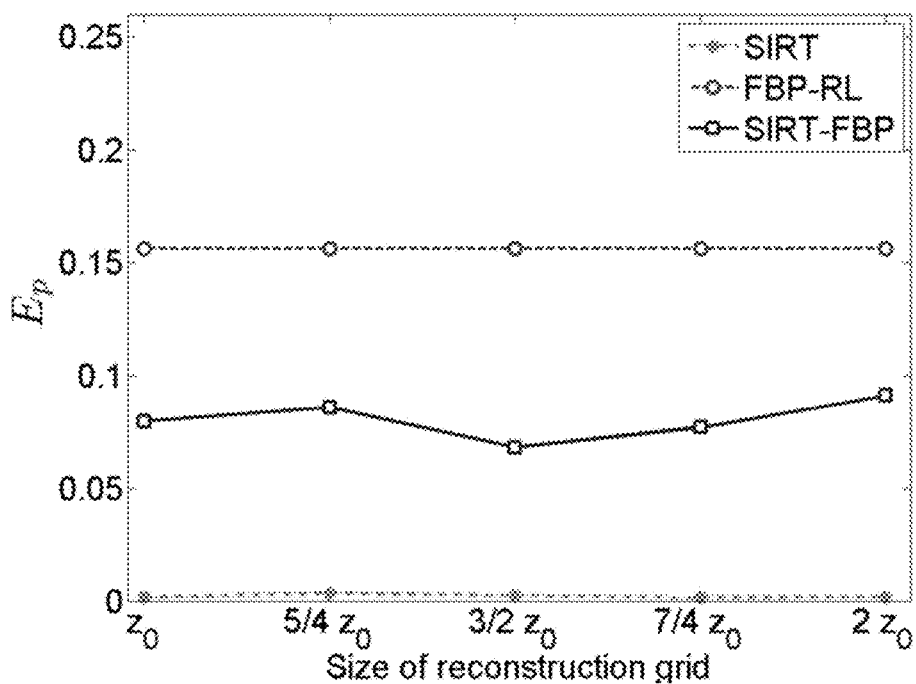
Figure 6G:
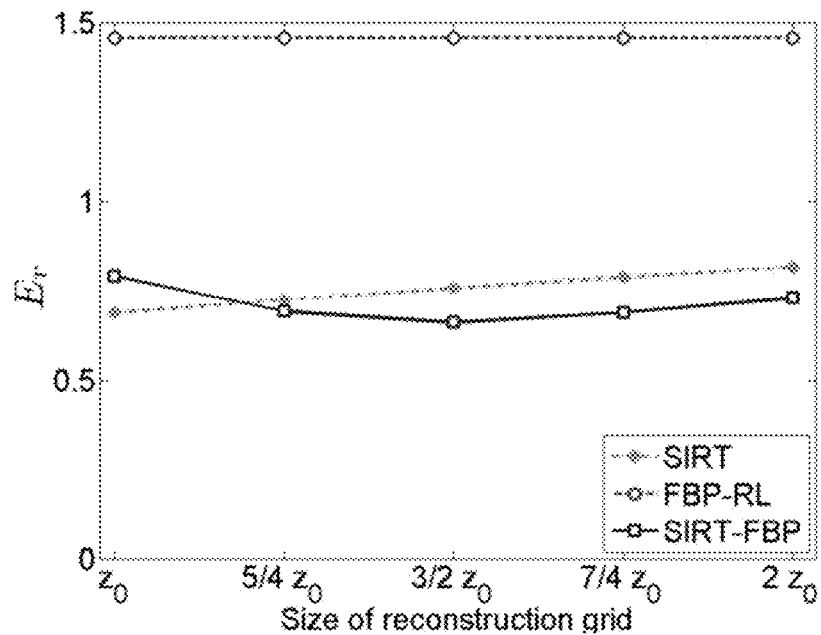
Figure 6H:
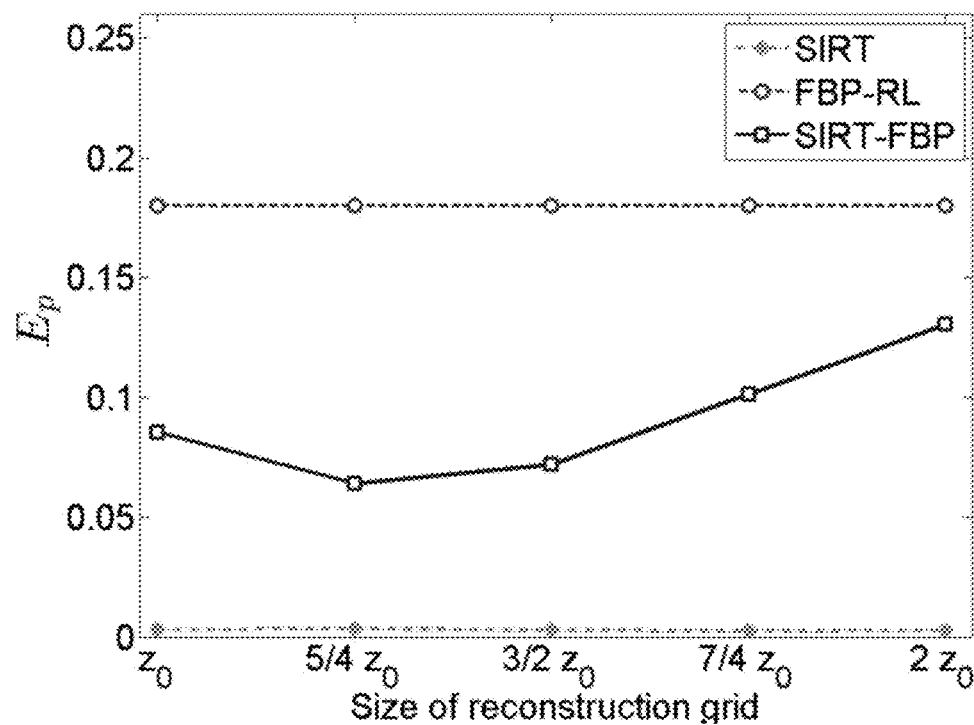
Figure 7A:
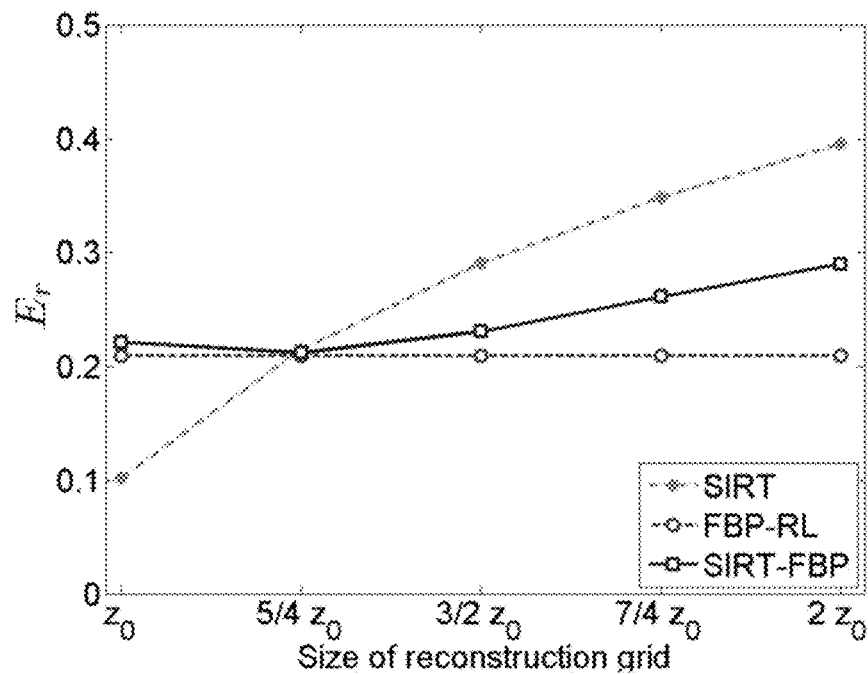
Figure 7B:
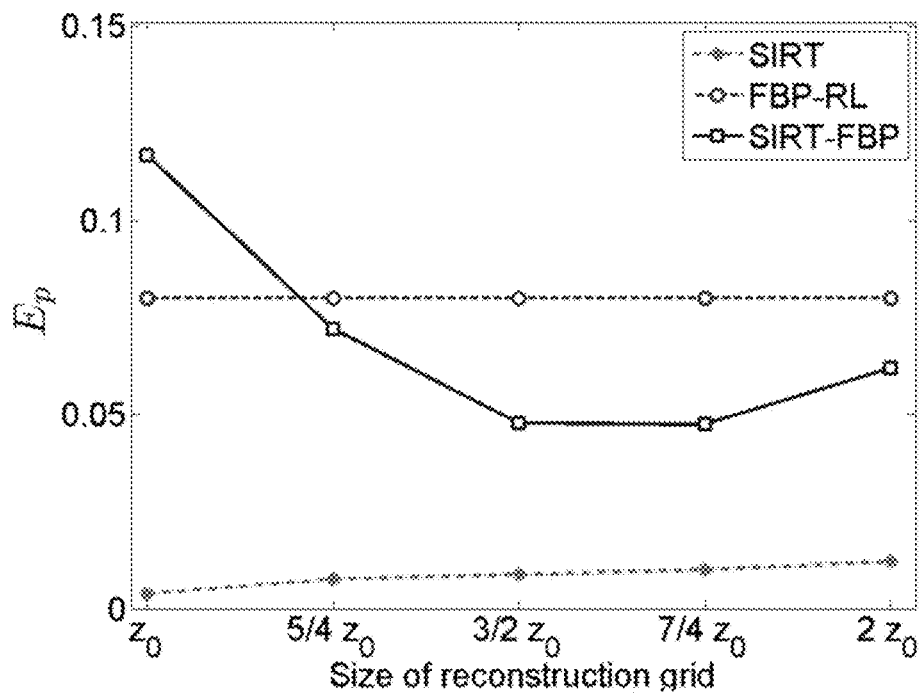
Figure 7C:
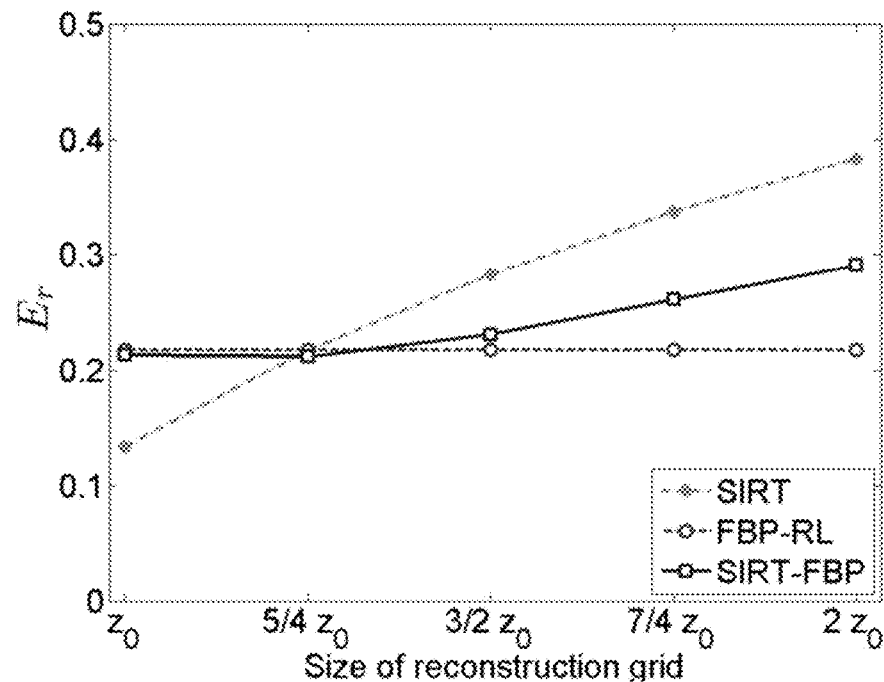
Figure 7D:
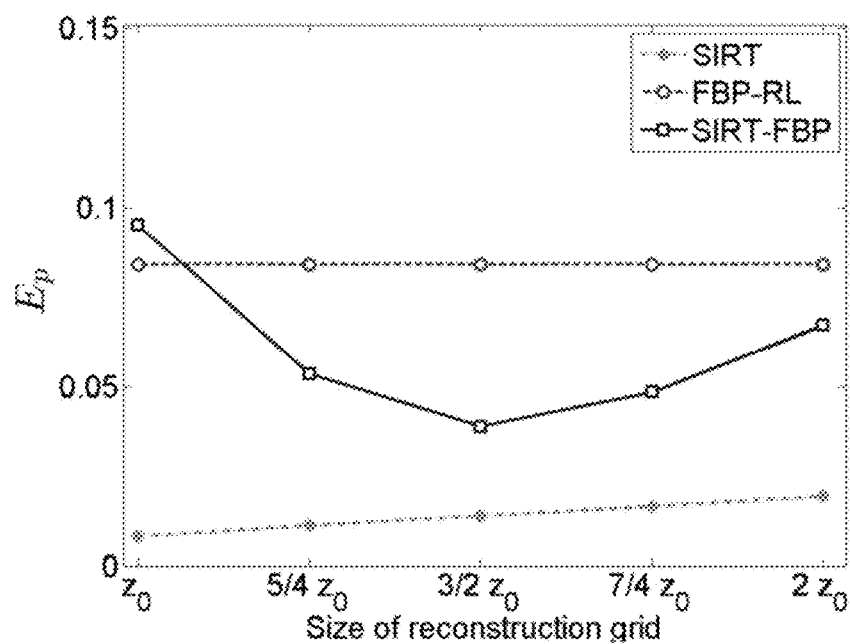
Figure 7E:
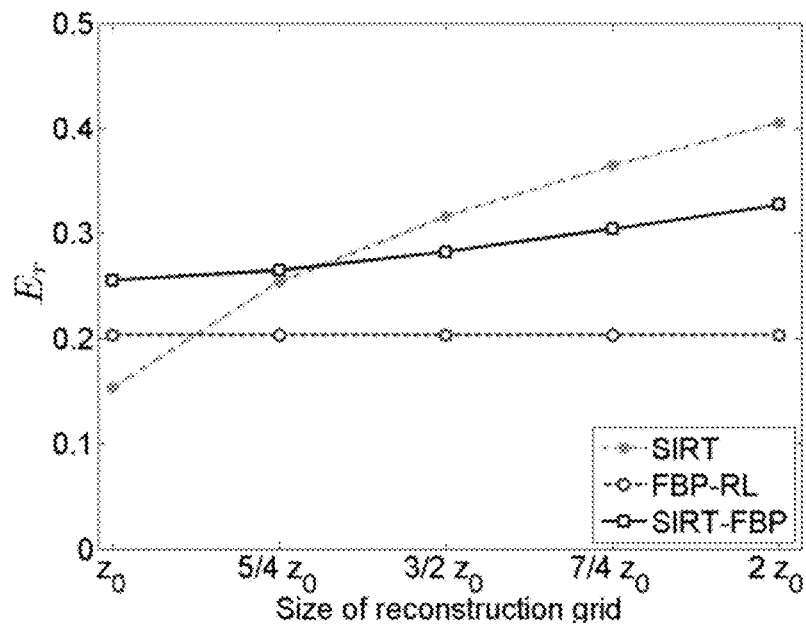
Figure 7F:
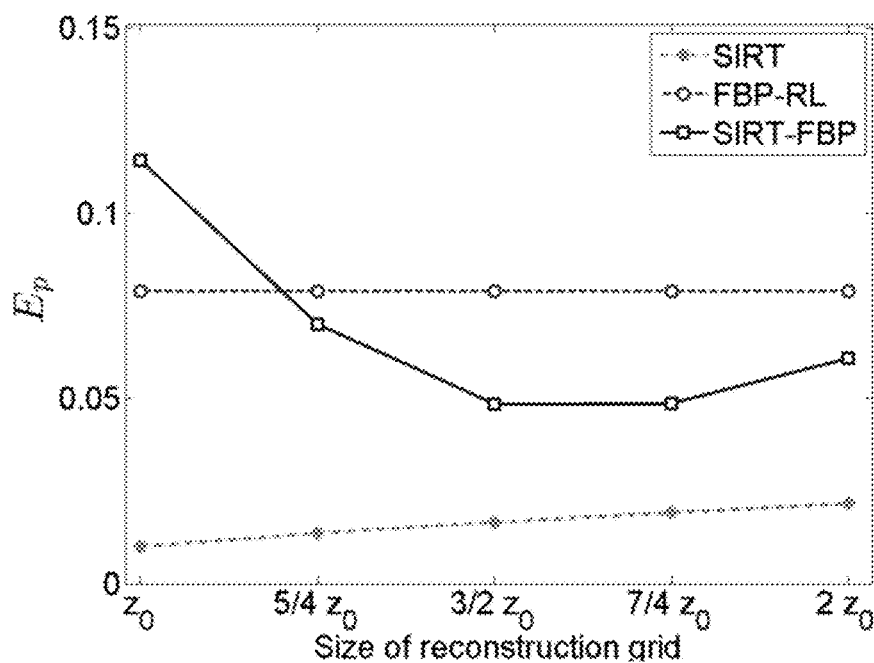
Figure 7G:
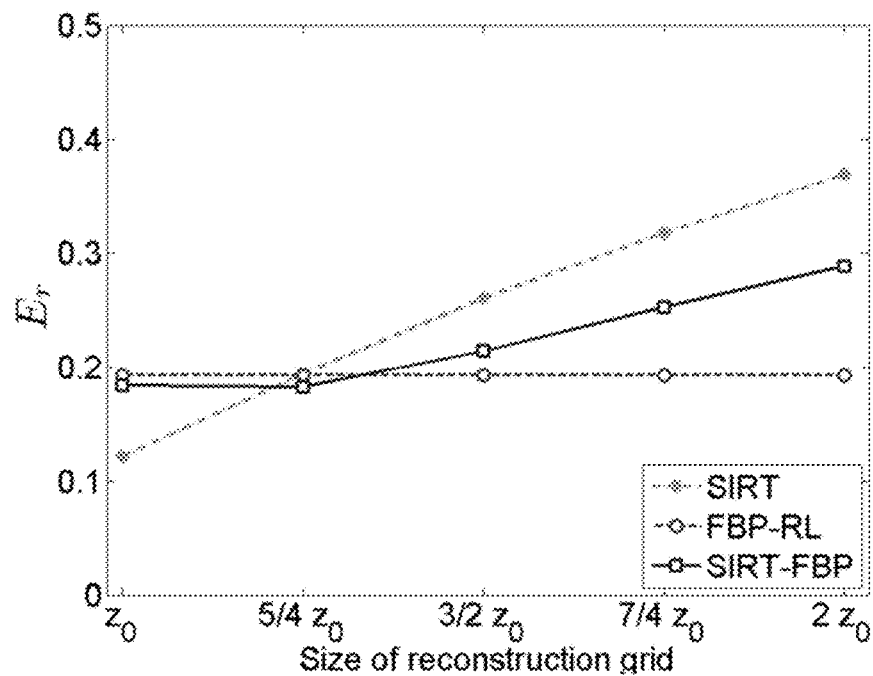
Figure 7H:
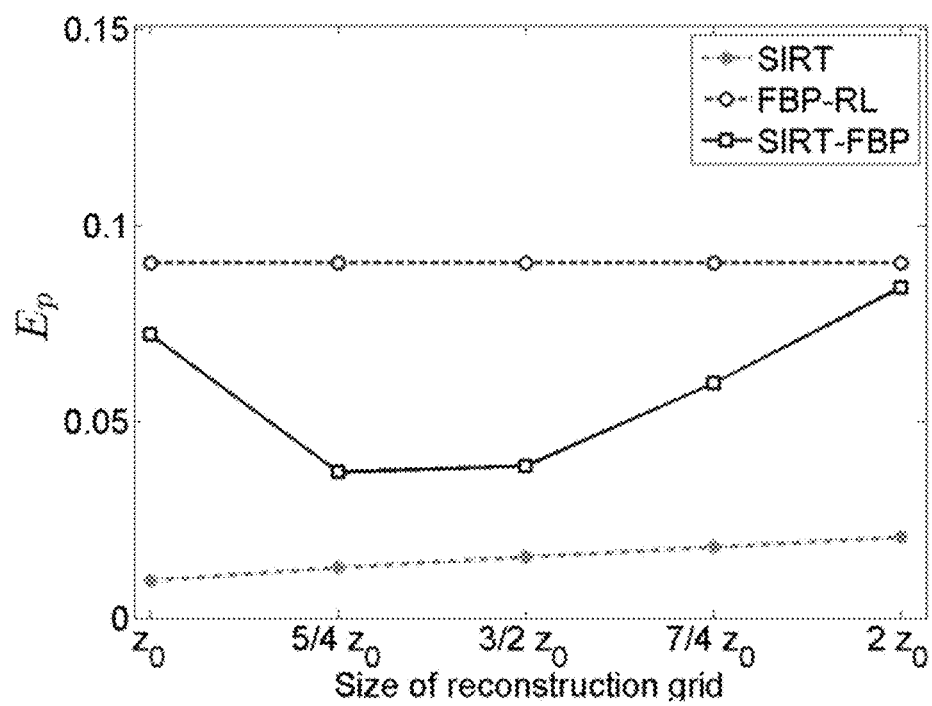

The reconstruction accuracy of the methods disclosed herein will further be illustrated using a series of illustrative examples. Four phantom images have been used for the illustrative examples, shown in FIG. 5, namely the well-known Shepp-Logan phantom, which is a superposition of 10 ellipses, a cross-section of a cylinder head in a combustion engine, a metal foam, and a part of a human mandible. The metal foam phantom and the human mandible phantom are slightly adjusted reconstructions of experimental μCT data sets. The size of all phantoms was $z_0 \times z_0 = 2044 \times 2044$ pixels. The projection data for these phantoms corresponded to parallel beam projections at regularly distributed angles over 180°. The number of projection angles was experimentally varied. The detector consisted of 511 bins, each having a width of four image pixels. The size of the detector therefore equaled the width of the phantoms. The Joseph kernel was used to determine the contribution of an image pixel to each ray. Per detector bin, four samples were taken, thereby ensuring that each image pixel participated with strictly positive weight.

For comparison purposes, the four phantoms were reconstructed using three reconstruction algorithms, SIRT (corresponding to the algorithm discussed hereabove, with ω=1, K=200, $\alpha(x)=\beta(x)=1/x$), FBP-RL (filtered backprojection with the standard Ram-Lak filter) and SIRT-FBP (filtered backprojection with a filter according to the present invention, in the present example obtained using the SIRT algorithm). Several series of experiments were performed to examine the relative reconstruction accuracy of the algorithms. A square reconstruction grid of z×z pixels was used during the experiments. Experiments showed that in some cases a reconstruction grid with z larger than the number of bins of the detector improved the accuracy of SIRT-FBP. The quality of the reconstruction methods was compared using the L1 norm of the differences between the phantoms and the reconstructions as a measure of the error.

In the first series of examples, the effect of the size of the reconstruction grid on the reconstruction accuracy of the algorithms was demonstrated. In a first run, 32 projection angles were used, while in a second run 256 projection angles were used. The accuracy of the reconstruction is shown in FIG. 6a to FIG. 6h and FIG. 7a to FIG. 7h for the first and second run respectively, where in FIGs a, c, e, g the mean reconstruction errors are shown (object space) and in FIGs b, d, f, h the projection errors are shown (projection space) for the different phantoms. The errors of the FBP-RL reconstructions are invariant under the size of the reconstruction grid z, while the errors of the SIRT reconstructions increase monotonically with increasing size of the reconstruction grid z. The results show that the mean reconstruction errors of SIRT-FBP are minimal on a size of the reconstruction grid z between $z_0$ and $3/2.z_0$. For larger grid sizes, the decreasing quality of the SIRT reconstructions determines the behavior of the errors of the SIRT-FBP reconstructions. The minimal mean projection error occurs close to reconstruction grid size $z=3/2.z_0$, and the error of SIRT-FBP for this grid size is significantly less than the mean projection errors of FBP-RL. Furthermore, the quality of the SIRT-FBP reconstructions with 32 projections exceeds that of FBP-RL and SIRT on grids with z between $5/4.z_0$ and $7/4.z_0$. Such results are not to be expected for 256 projections, since FBP-RL outperforms SIRT on these grids. Still, it can be seen that SIRT-FBP is significantly better than SIRT on these grid sizes.

Figure 8:
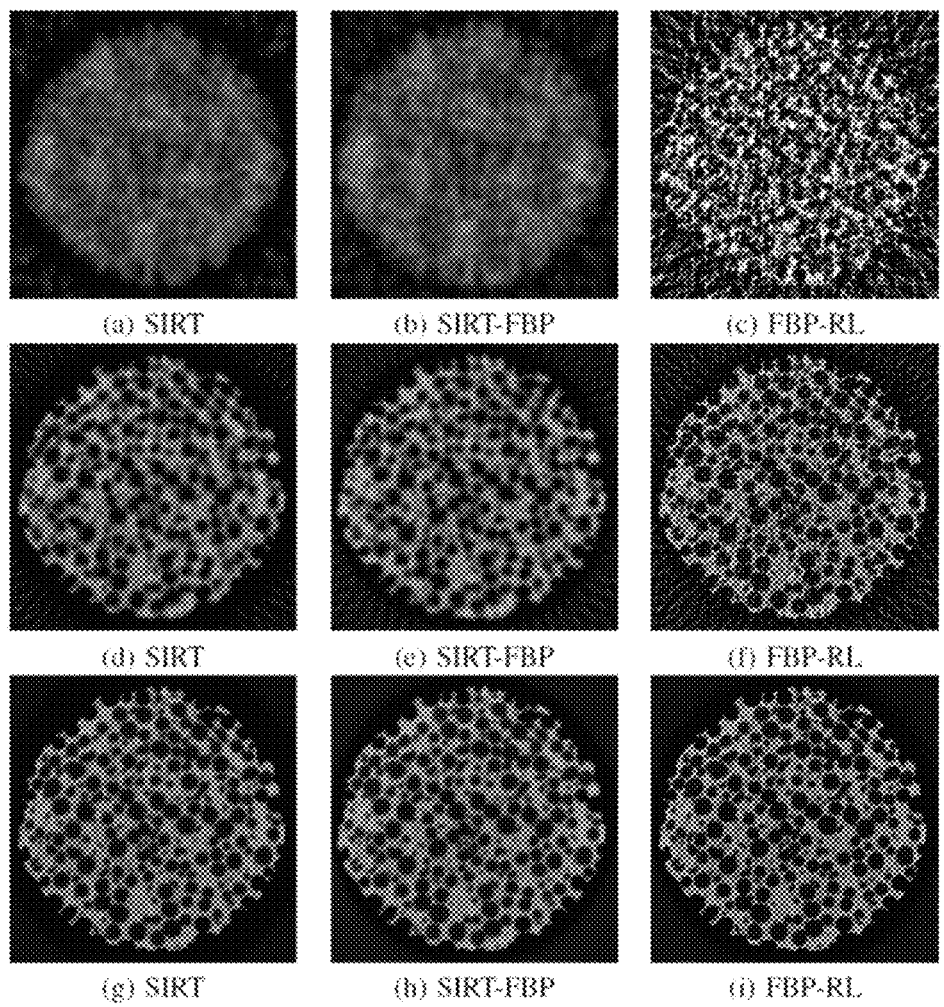
FIG. 8 illustrates a comparison of reconstructions of phantom 3 using different techniques for a varying number of projection angles, illustrating advantages of embodiments of the present invention.
Figure 9A:
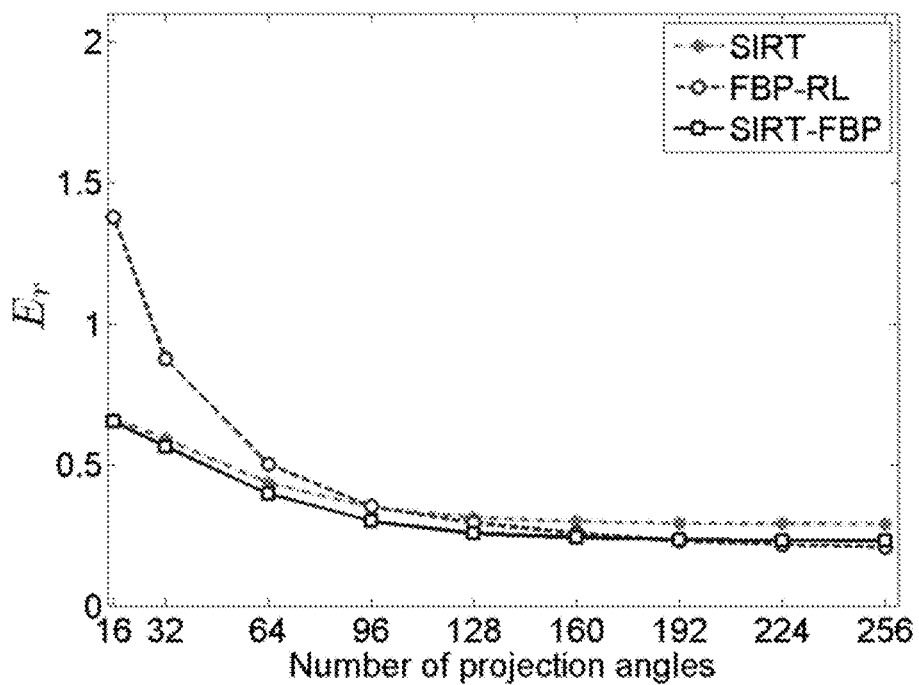
FIG. 9a to FIG. 9h and FIG. 10a to FIG. 10h show the accuracy (reconstruction errors and projection errors) as a function of the number of projection angles respectively as a function of the angular range used for different reconstruction techniques, illustrating advantages of embodiments of the present invention.
Figure 9B:
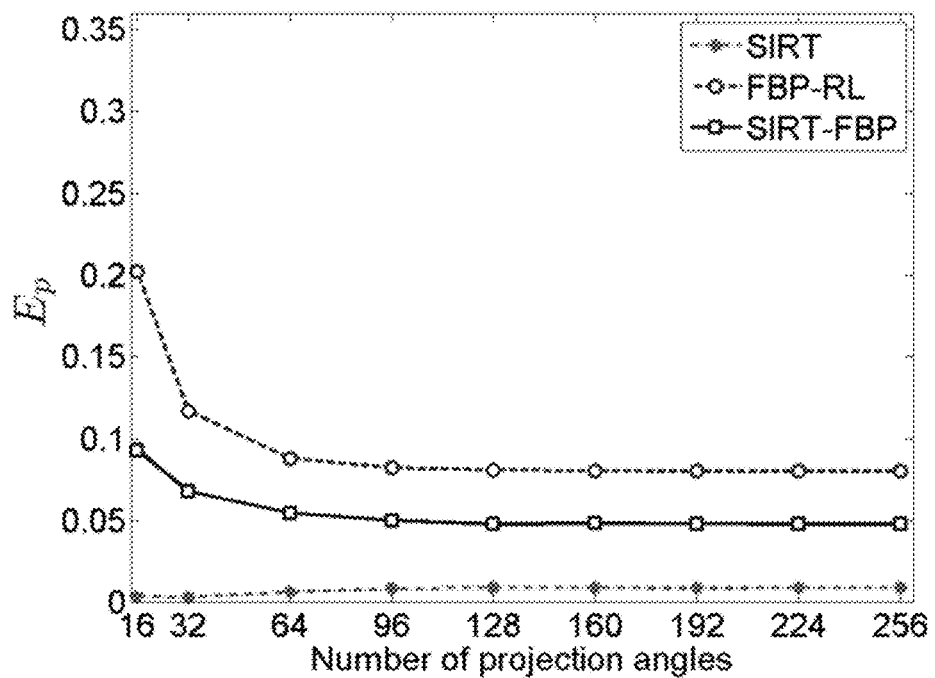
Figure 9C:
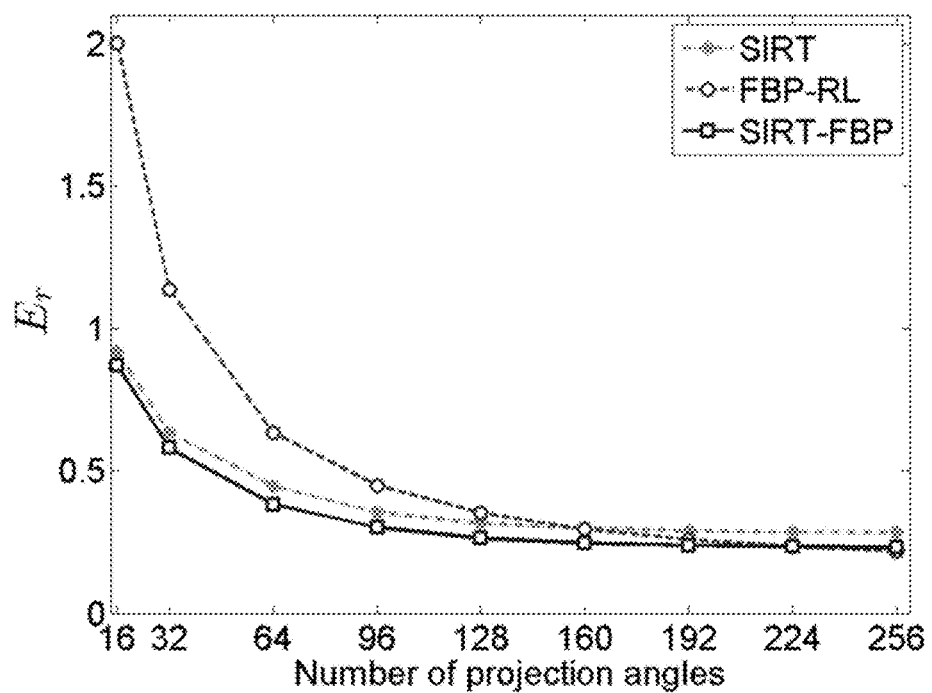
Figure 9D:
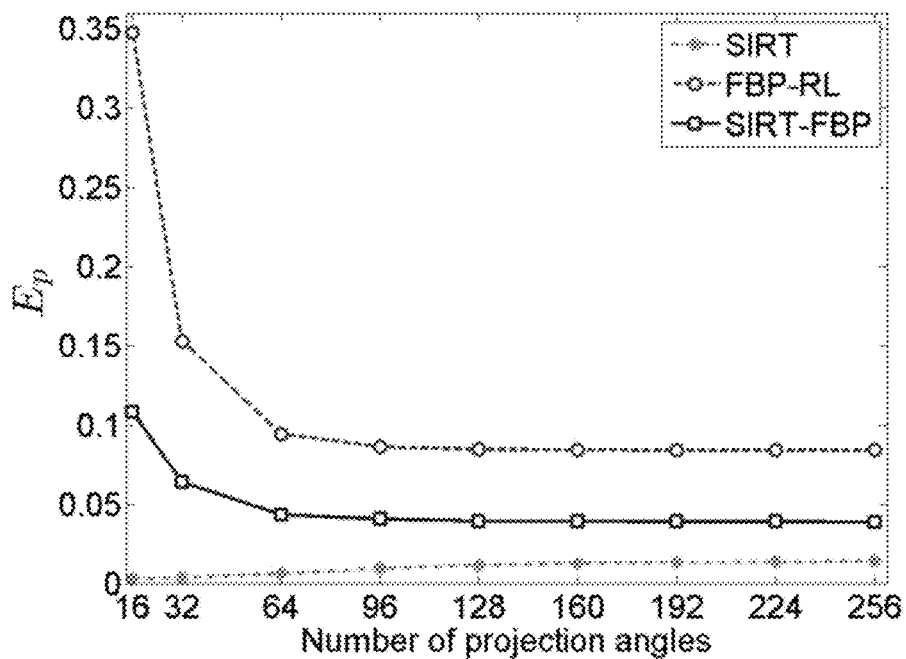
Figure 9E:
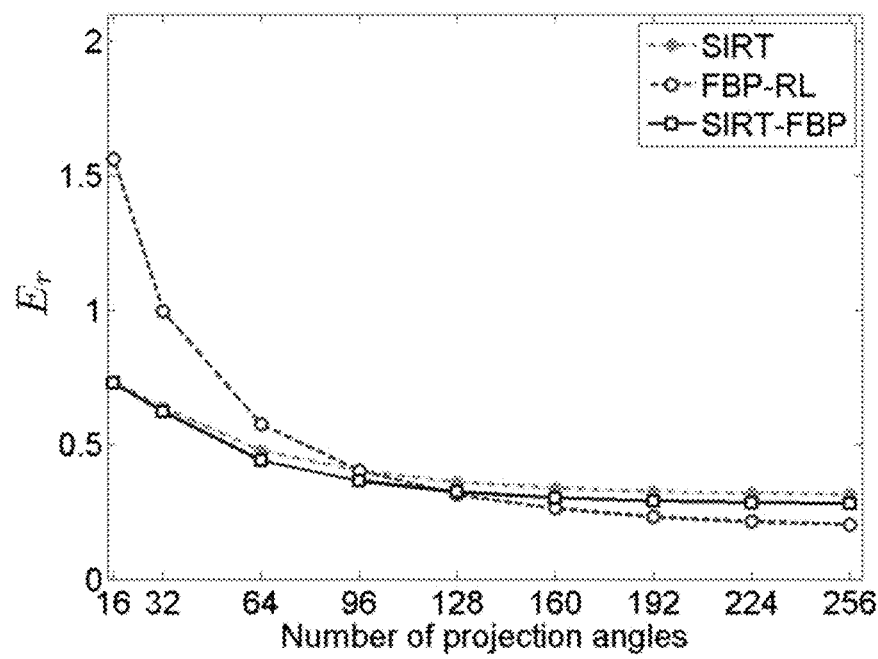
Figure 9F:
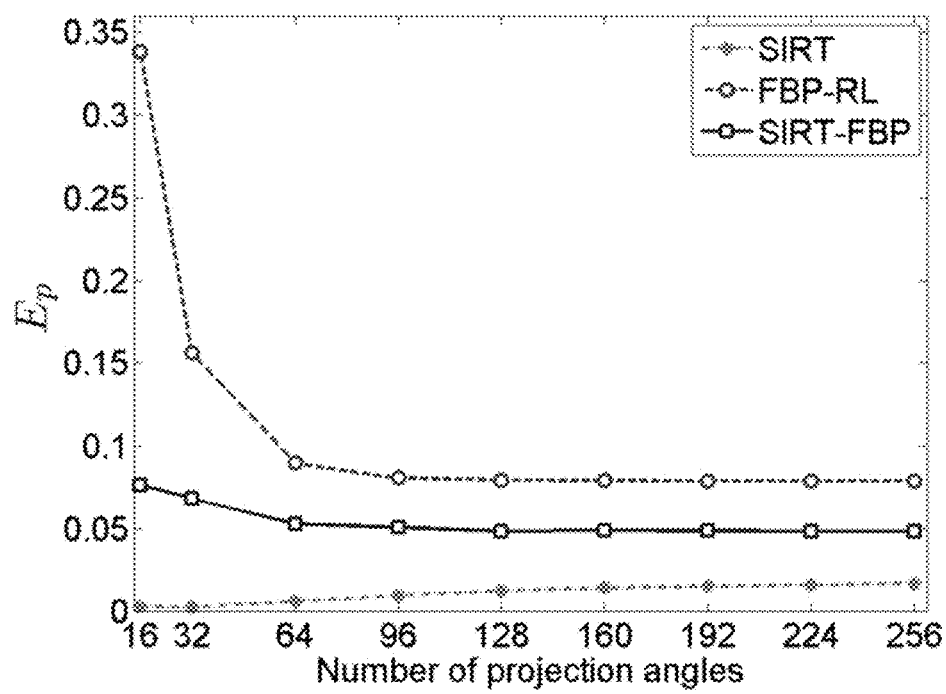
Figure 9G:
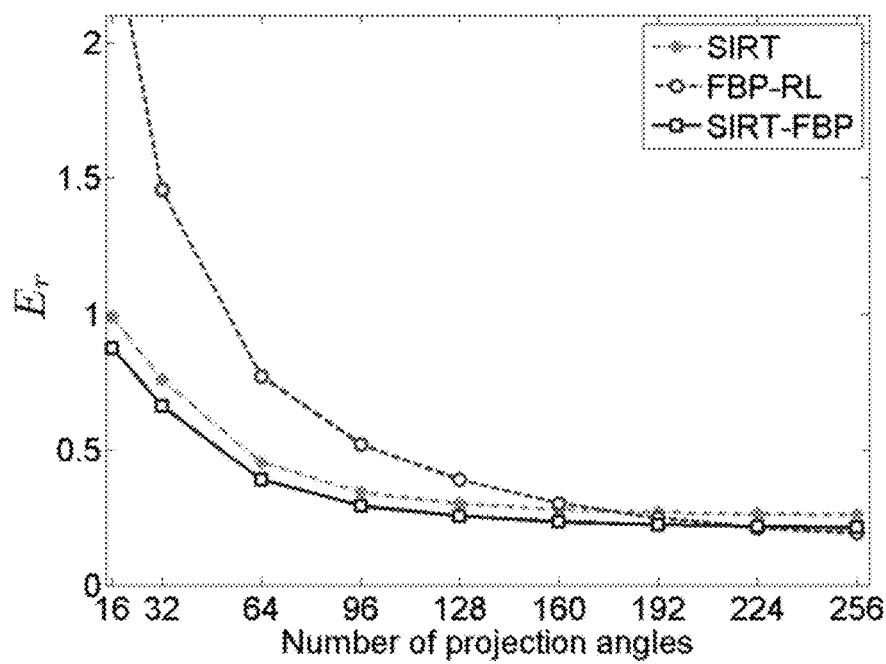
Figure 9H:
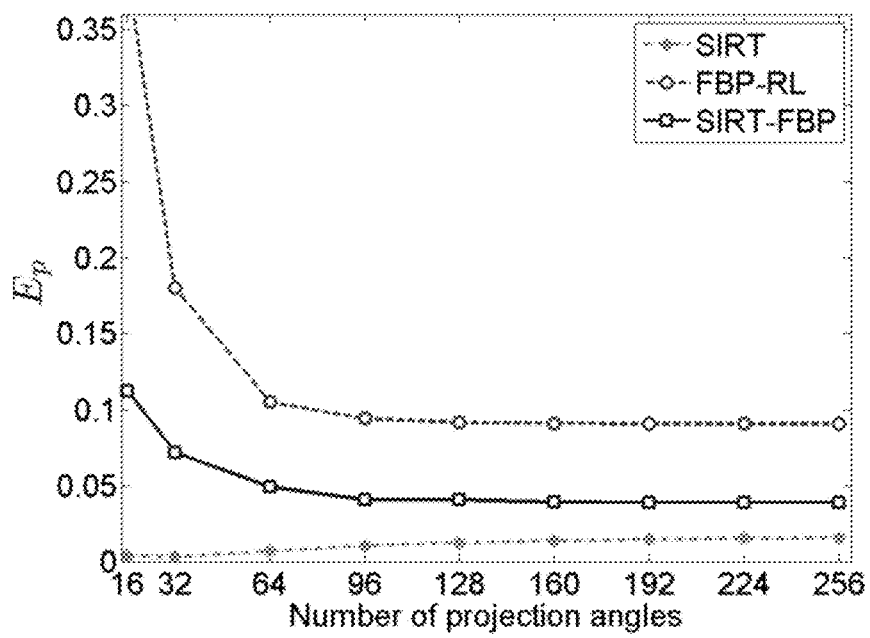
Figure 10A:
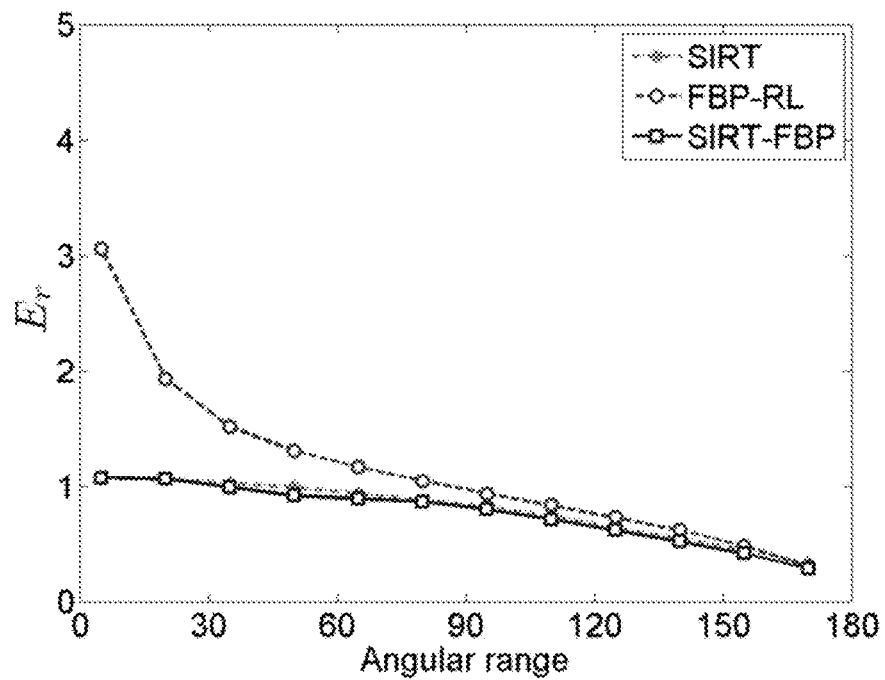
Figure 10B:
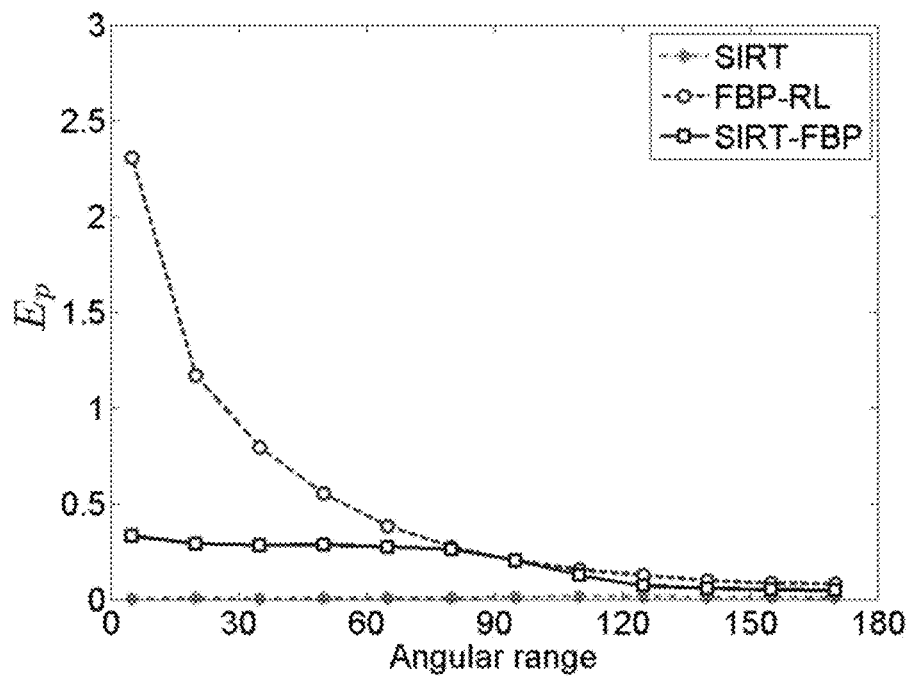
Figure 10C:
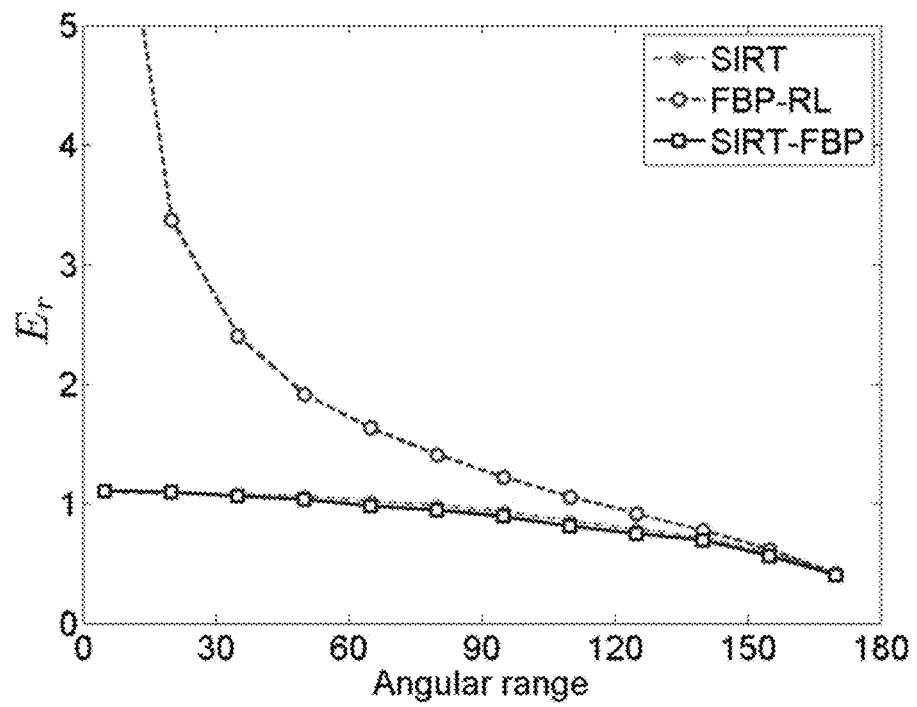
Figure 10D:
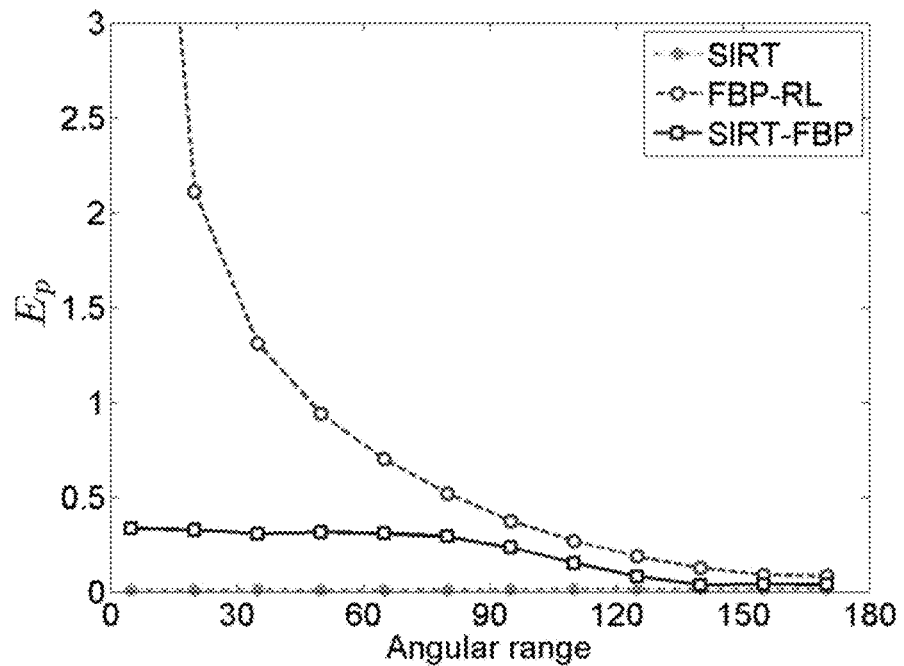
Figure 10E:
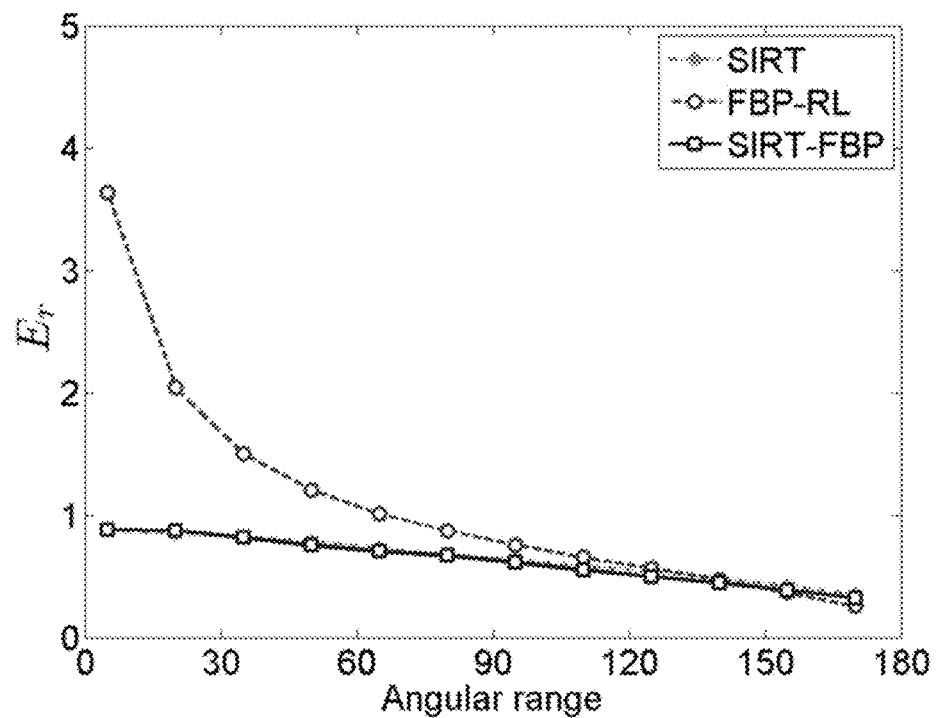
Figure 10F:
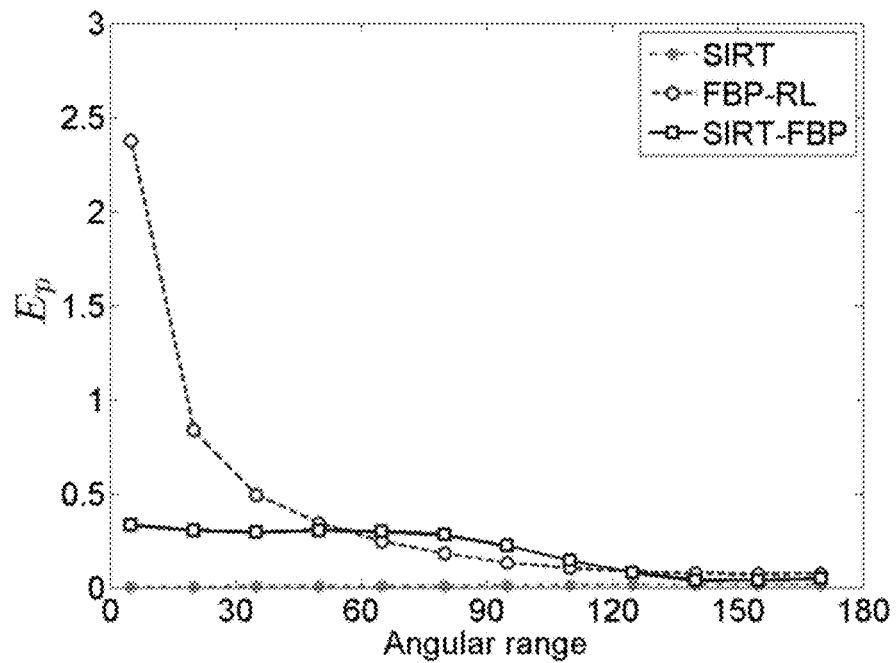
Figure 10G:
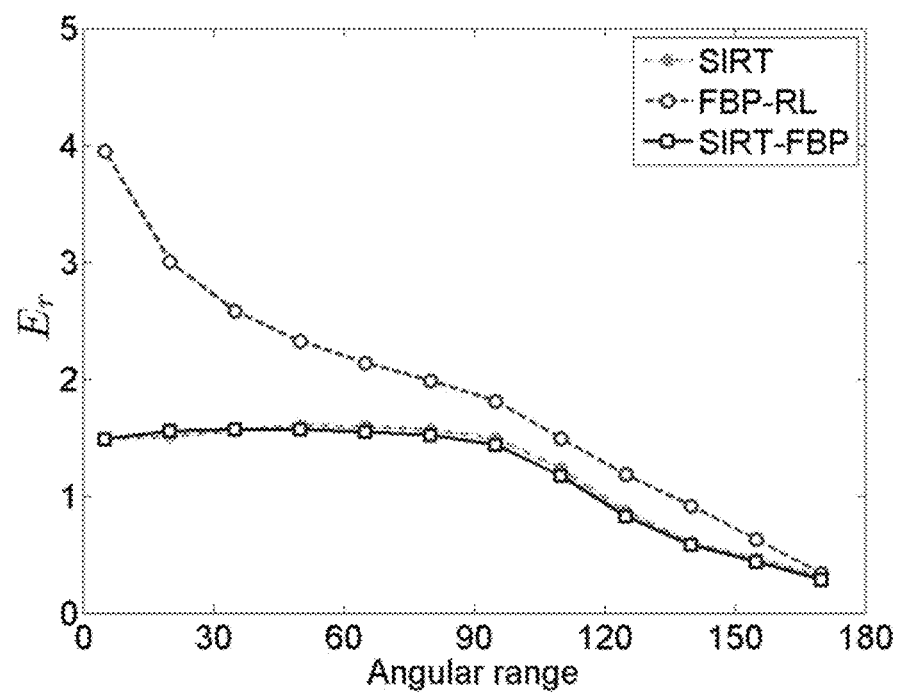
Figure 10H:
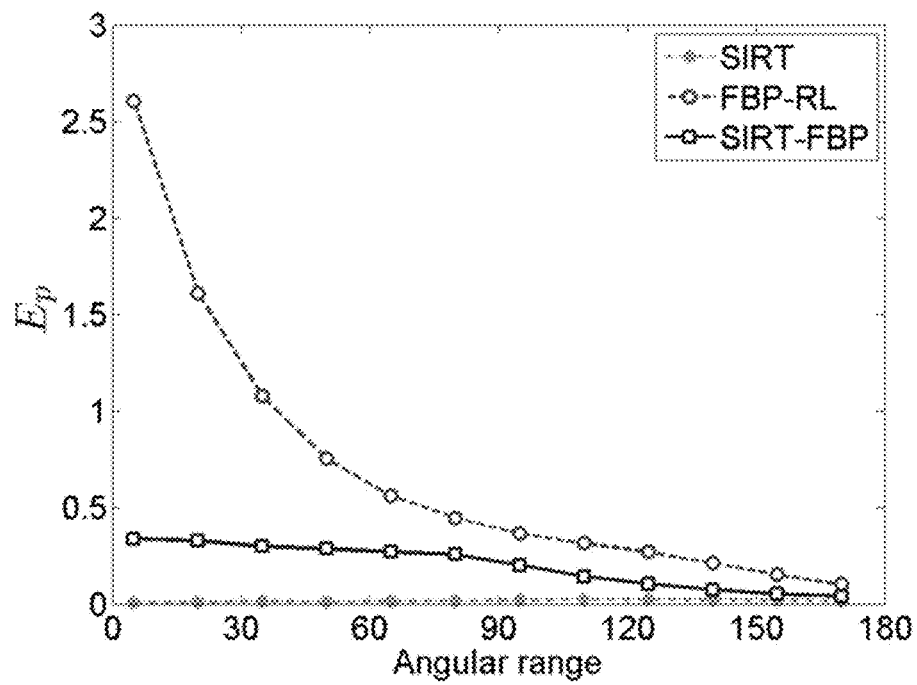

In the second series of examples, the size of the reconstruction grid was kept fixed and the accuracy was examined as a function of the number of projection angles. In certain applications, e.g. electron tomography, the angular range can be limited which can severely degrade the quality of the reconstructions. Therefore, the accuracy of the reconstruction was also examined for a situation with limited angular range. The number of projection angles was varied between 16, 64 and 256 angles, while z was kept fixed. Some reconstructions of phantom 3 are shown in FIG. 8 where $z=3/2.z_0$ is chosen based on the results of previous experiments. The result for 16 angles is shown at the top, the result for 64 angles is shown in the middle and the result for 256 angles is shown at the bottom. FIG. 9a to FIG. 9h shows that, for all considered numbers of projection angles, the forward projections of SIRT-FBP reconstructions were more accurate than those of FBP-RL reconstructions. For most phantoms, the SIRT-FBP reconstructions are also more accurate than the FBP-RL reconstructions when the number of projections is at most 192. Again in FIGs a, c, e, g the reconstruction errors are shown whereas in FIGs b, d, f, h the projection errors are shown.

Figure 11:
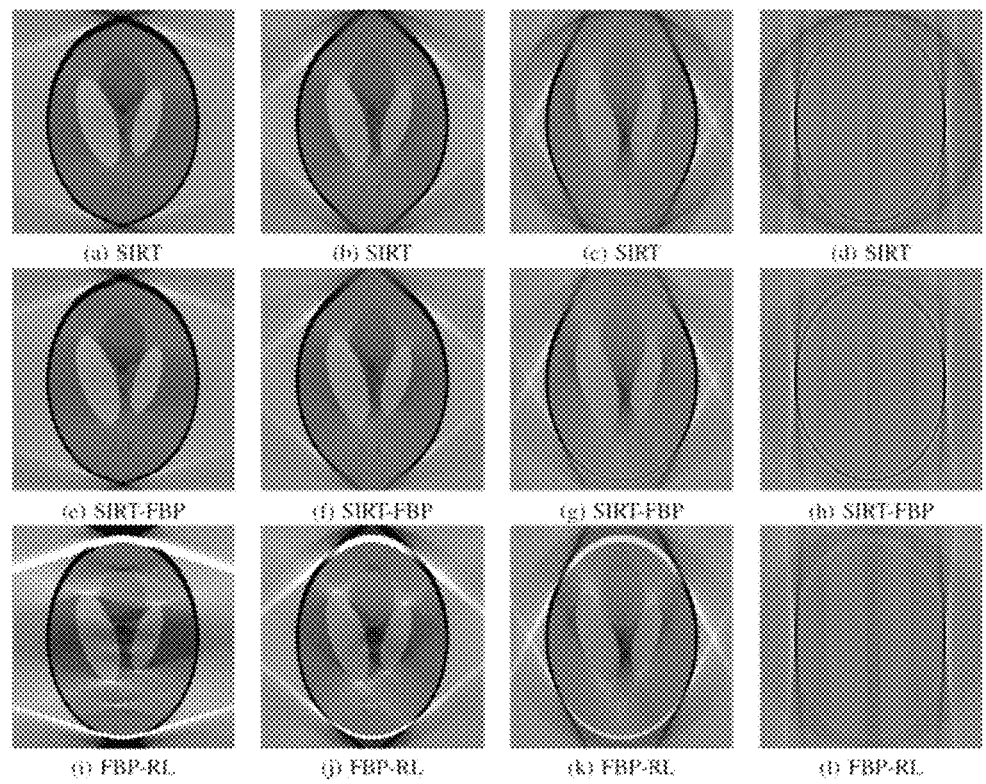
FIG. 11 illustrates the difference between the original image and the reconstruction of phantom 1 for different techniques as function of the angular range used (from left to right 35, 80, 125, 170 degrees), illustrating advantages of embodiments of the present invention.

The results shown in FIG. 10a to FIG. 10h show the accuracy of the reconstruction algorithms when the angular range was limited. The distance between two consecutive angles was 0.5 degree, and an angular range of 180° corresponded to full angular range with d=360. In FIGS a, c, e, g the reconstruction errors are shown whereas in FIGs b, d, f, h the projection errors are shown. FIG. 11 shows the difference between phantom 1 and its reconstructions for a selection of the considered limited angular ranges. The error in the forward projections was calculated using only those projections that were included in the angular range. The results show that the errors of SIRT-FBP reconstructions are similar to those of SIRT reconstructions, while for an angular range below 150° the errors of SIRT-FBP were much smaller than the errors of FBP-RL for all phantoms. The quality of the forward projections of SIRT-FBP reconstructions is almost everywhere higher than that of FBP-RL reconstructions.

Figure 12:
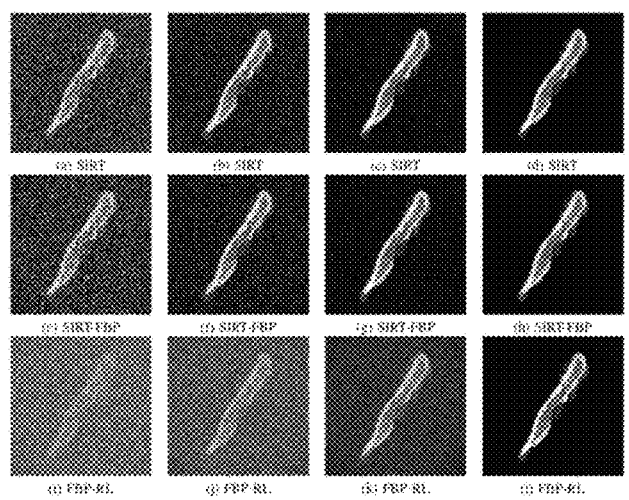
FIG. 12 illustrates reconstruction of phantom 4 for different reconstruction techniques as a function of varying noise levels (from left to right: 250, 1000, 50000, $10^6$)
Figure 13A:
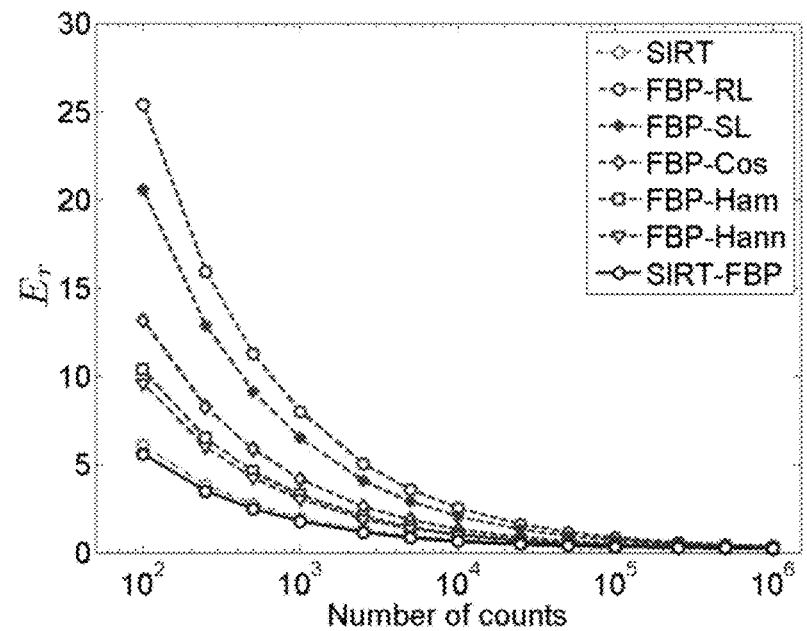
FIG. 13a to FIG. 13h illustrates the reconstruction errors for different reconstruction techniques as a function of the amount of noise in the projection angles, illustrating advantages of embodiments of the present invention.
Figure 13B:
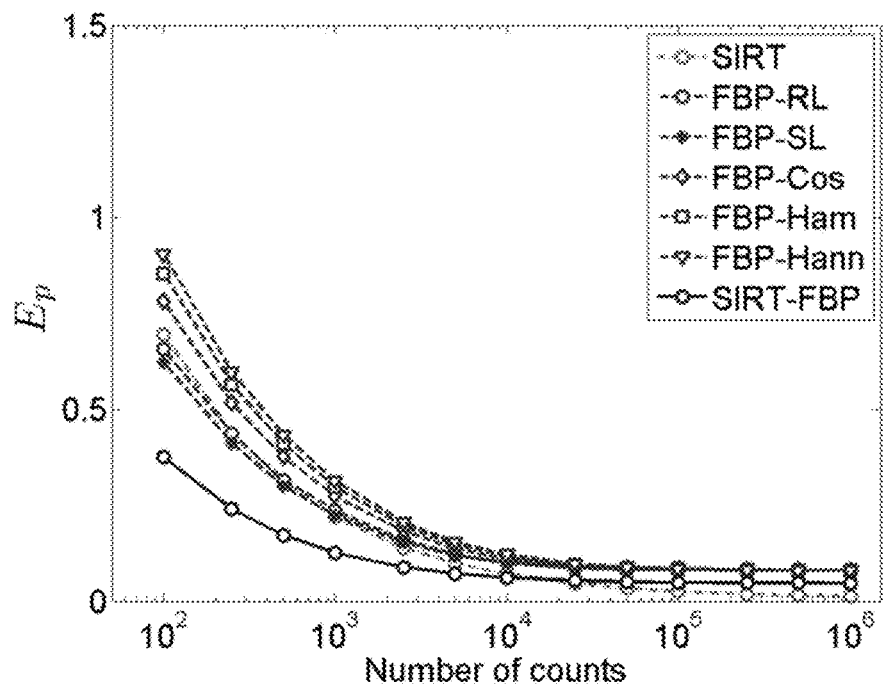
Figure 13C:
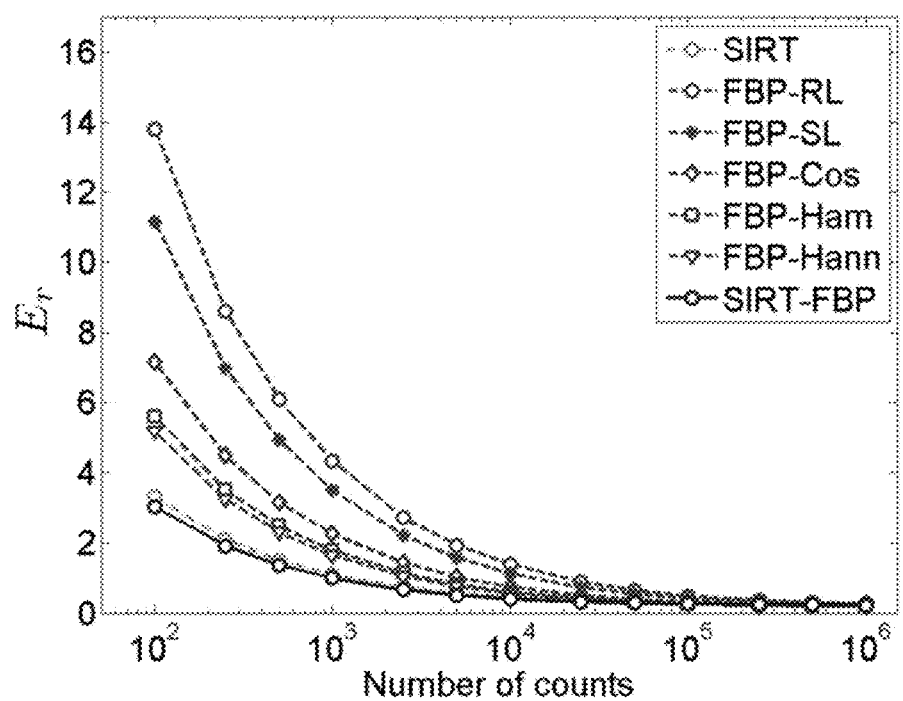
Figure 13D:
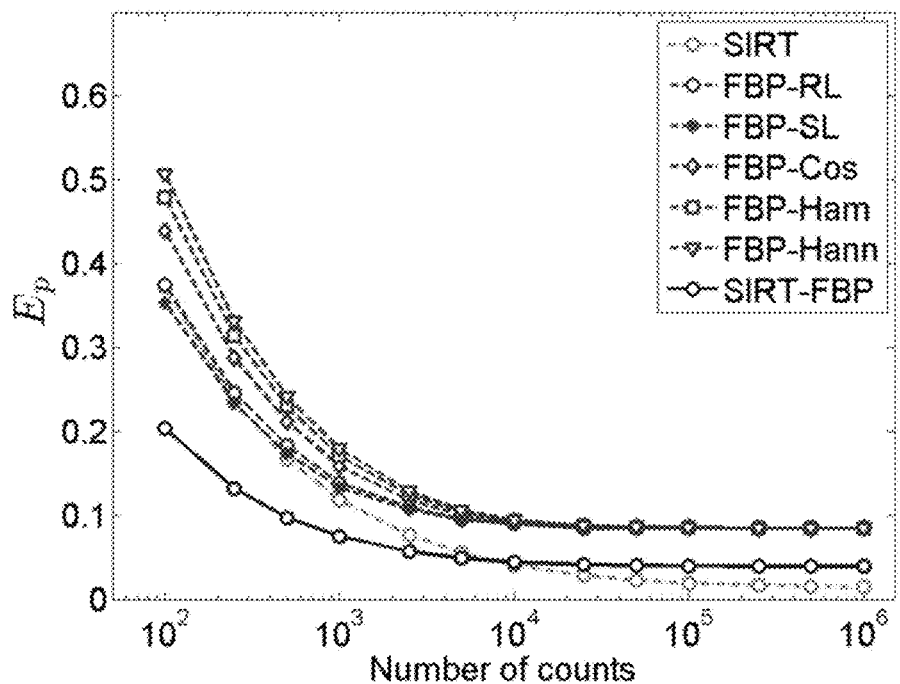
Figure 13E:
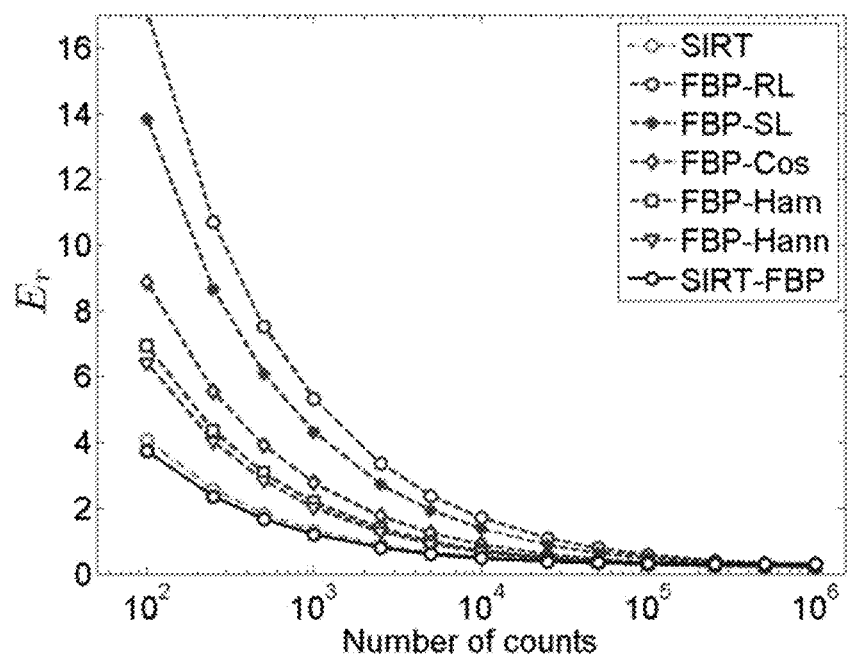
Figure 13F:
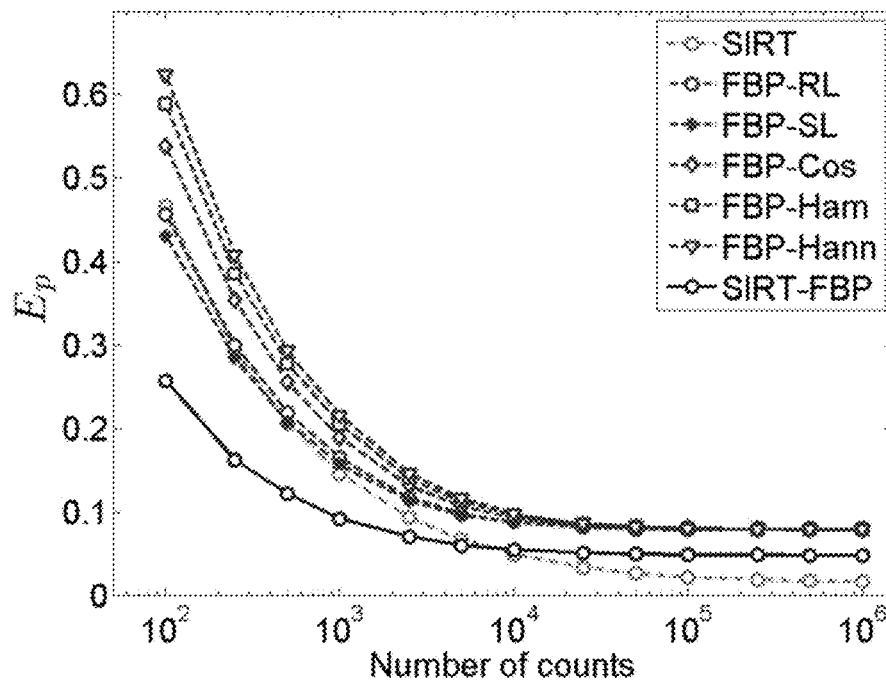
Figure 13G:
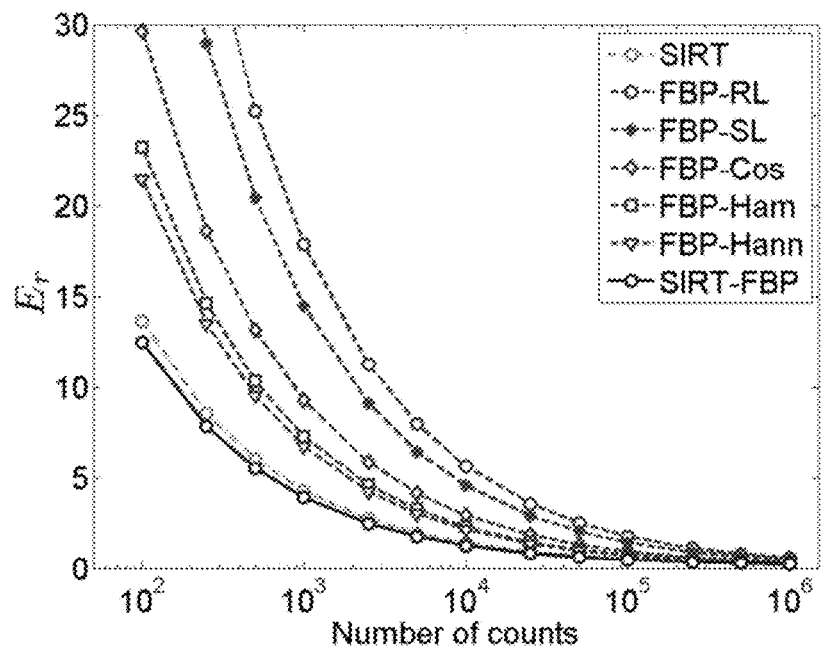
Figure 13H:
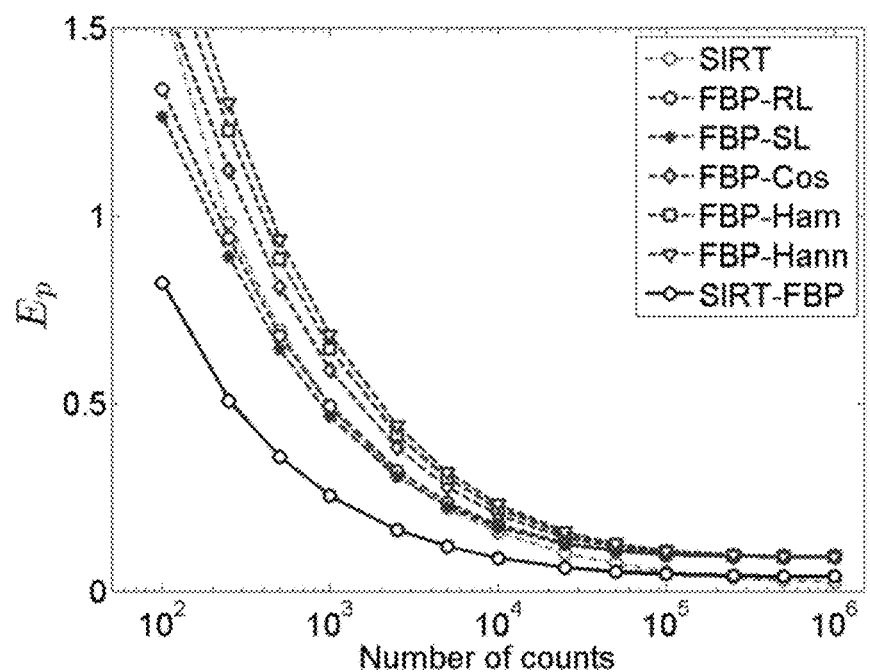

In the third series of examples, the robustness of the reconstruction algorithms with respect to noise is demonstrated. All experiments so far were performed using noiseless projection data. FBP-RL is known to produce poor quality reconstructions from projection data that are highly polluted with noise, while SIRT handles this data relatively well. In this series the accuracy of SIRT-FBP was compared to FBP-RL and SIRT in case of noisy projection data. Noiseless projection data were obtained with d=256 and full angular range. Poisson distributed noise with varying $I_0$, number of counts per detector element, was applied to this data, where $I_0$ ranges from $10^2$ to $10^6$. Some reconstructions are shown in FIG. 12. Since the accuracy of FBP with the standard Ram-Lak filter is known to be less than that of other well-known standard filters for noisy projection data, the errors of the following filters are also shown: Shepp-Logan, Cosine, Hamming and Hann.

The results in FIG. 13 show that the errors between the reconstructions of SIRT-FBP and SIRT were very similar and that the quality of (the forward projections of) SIRT-FBP was significantly higher than that of FBP reconstructions with any standard filter used in this experiment. In FIGS a, c, e, g the reconstruction errors are shown whereas in FIGs b, d, f, h the projection errors are shown.

Figure 14:
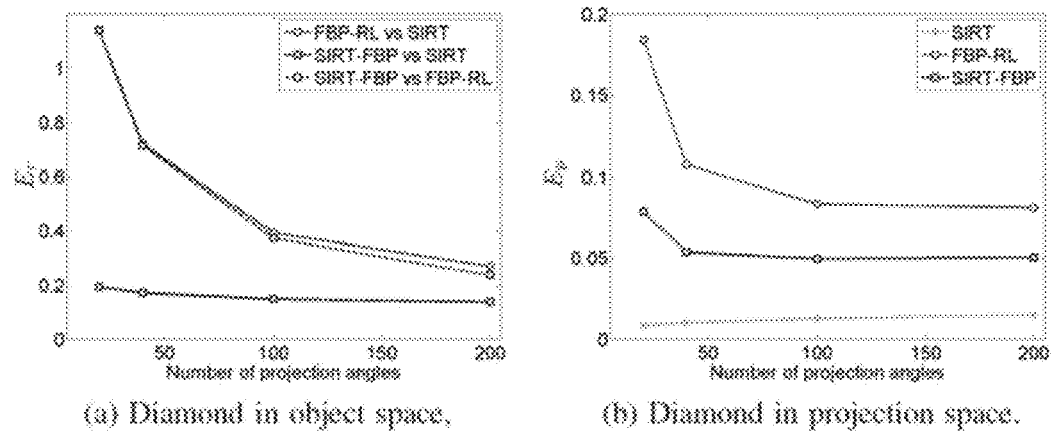
FIG. 14 illustrates the reconstruction errors for different reconstruction techniques as a function of the number of projection angles for experimental μCT data, illustrating advantages of embodiments of the present invention.
Figure 15:
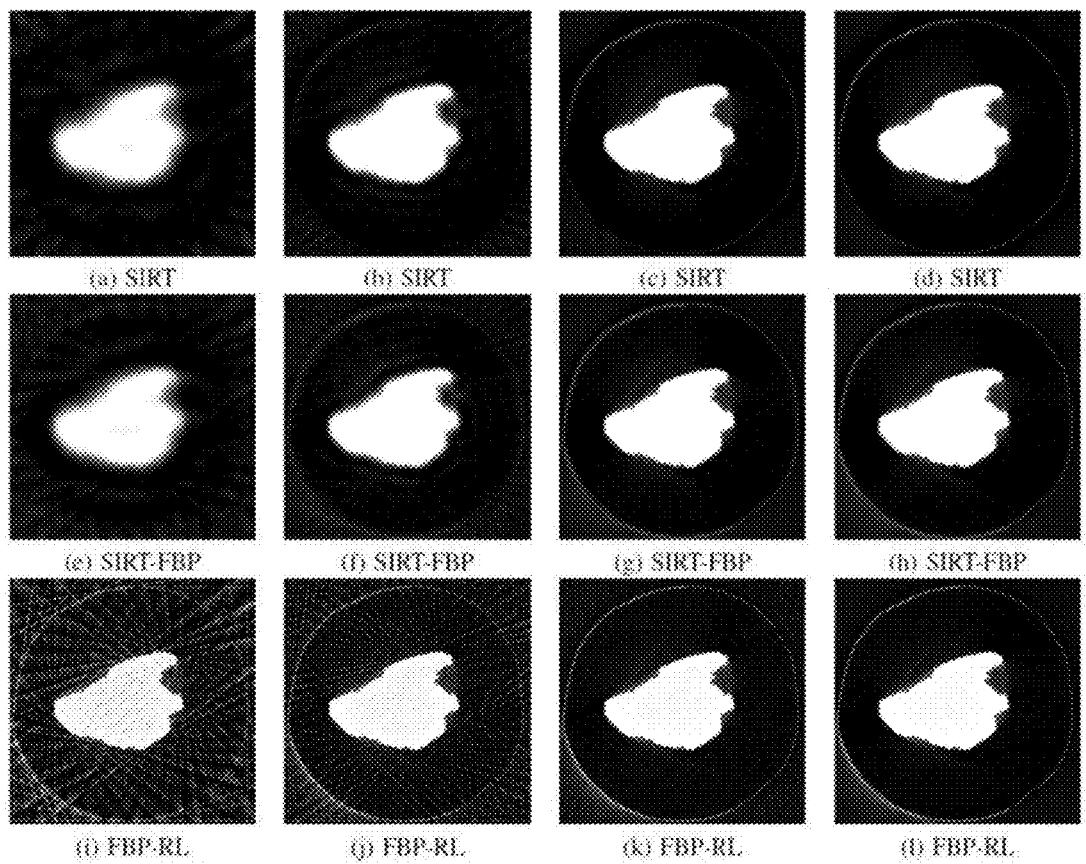
FIG. 15 illustrates diamond reconstruction for experimental μCT data for different reconstruction techniques for a different number of projections (from left to right: 20, 40, 100, 200).
Figure 16A:
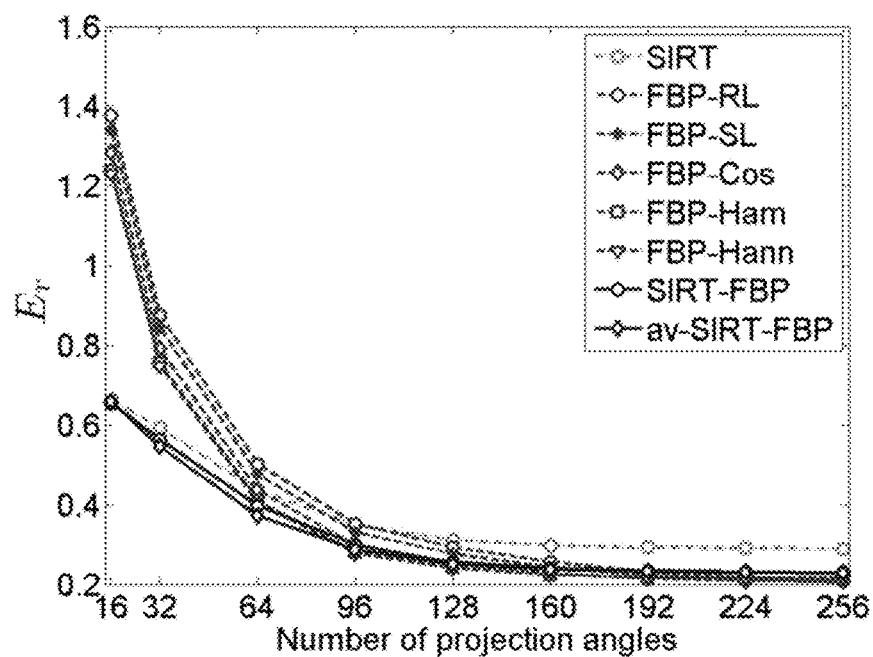
FIG. 16a to FIG. 16d illustrate reconstruction and projection errors for filtered back projection for different reconstruction techniques in object space (left) and in projection space (right) for the first and second phantom, illustrating advantages of embodiments of the present invention.
Figure 16B:
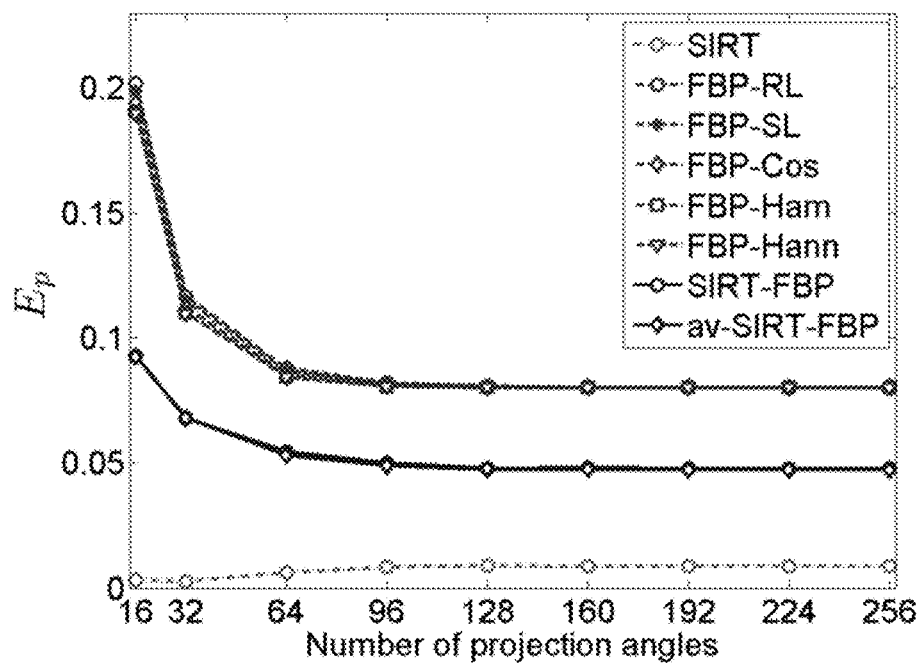
Figure 16C:
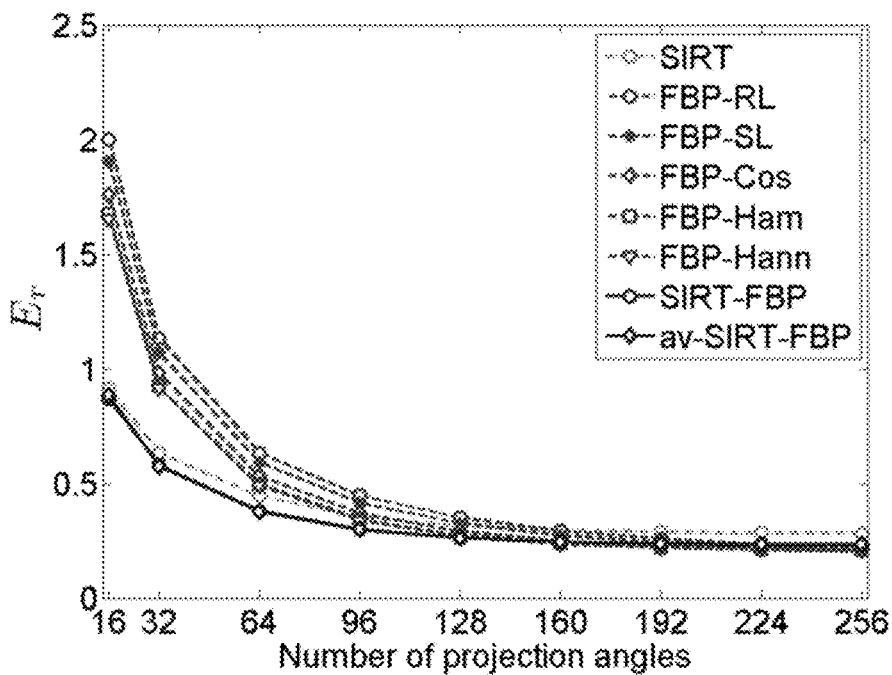
Figure 16D:
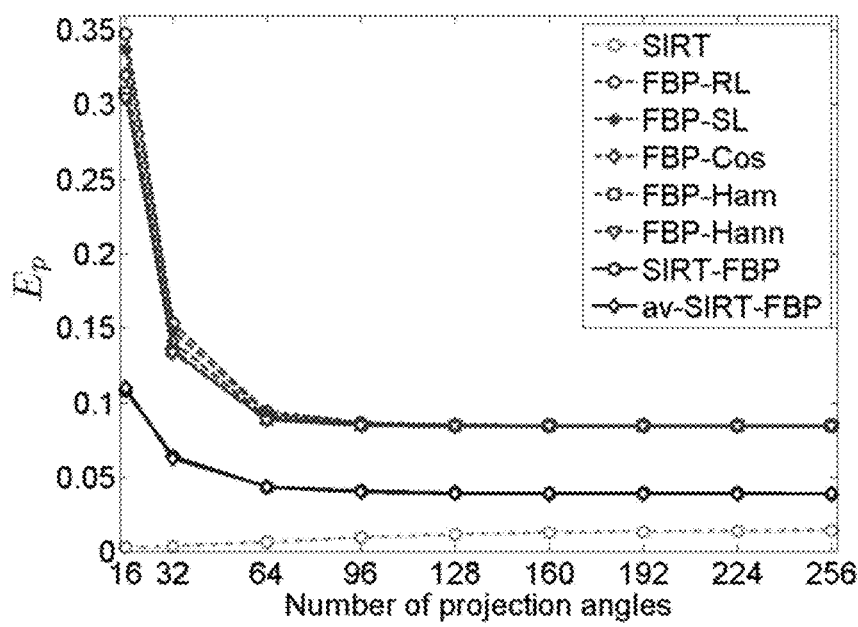

The fourth series of examples examines the accuracy of the reconstruction methods when reconstructing an experimental μCT data set. The data represents a slice of a diamond scanned with a μCT scanner. Since the original phantom was not available, the reconstructions were compared with each other to analyze the error behavior in the object space. The results in FIG. 14 show that the error of the SIRT-FBP reconstructions behaves very similar to that of SIRT reconstructions, while the difference between SIRT-FBP and FBP-RL reconstructions is comparable to that between SIRT and FBP-RL reconstructions. The reconstructions in FIG. 15 show the same behavior patterns. For low numbers of projection angles the mean projection error of SIRT-FBP is much less than that of FBP-RL.

In the fifth series of examples, the projection data were filtered with an angle independent filter. This way of filtering the projection data enables an implementation similar to filtered backprojection with a standard filter. The angle independent filter in these experiments was the average of the filters for all projection angles. The corresponding reconstruction algorithm is denoted by av-SIRT-FBP. Although the implementation of av-SIRT-FBP is similar to FBP with a standard filter, the quality of av-SIRT-FBP reconstructions was comparable to that of SIRT-FBP reconstructions, as can be seen in FIG. 16a to FIG. 16d for the phantoms 1 and 2. In FIGs a and c the reconstruction errors are shown, whereas in FIGs b and d the projection errors are shown. The reconstructions of phantoms 3 and 4 show similar patterns and are therefore not included.

From the above experimental results, it can be seen that the quality of reconstructions based on filters according to the present embodiments is similar to the quality of reconstructions based on a reconstruction algorithm. The latter supports the fact that for example in cases where filtered back projection with conventional filters are known to produce low quality reconstructions, reconstruction methods according to the present invention can be equally well applied than the use of algebraic reconstruction algorithms. The latter results in efficient reconstruction techniques.

The invention claimed is:

1. A method for applying in a tomographic imaging system a filter component for an analytical tomographic reconstruction technique used in tomographic imaging in the tomographic imaging system, the method comprising:
   obtaining an algebraic reconstruction algorithm for reconstructing a spatial representation of a volume of interest from a projection data set, the algebraic reconstruction algorithm taking into account a geometry of the tomographic imaging,
   applying the algebraic reconstruction algorithm to a plurality of virtual projection data sets to produce a plurality of reconstructed spatial representations, and determining the filter component using the plurality of reconstructed spatial representations,
   implementing the filter component in the tomographic imaging system, wherein each virtual projection data set correspond with a basis vector of a basis for the projection space.

2. A method according to claim 1, wherein determining of the filter component comprises combining values from the plurality of reconstructed spatial representations corresponding to at least one reference location in the space of the spatial representation of the volume of interest.

3. A method according to claim 1, wherein the plurality of virtual projection data sets comprises at least two non-zero elements corresponding to different projection angles according to said geometry of the tomographic imaging, so that determining comprises determining a filter component having dedicated components for each of the different projection angles.

4. A method according to claim 1, wherein the at least one reference location comprises the geometrical center of the volume of interest.

5. A method according to claim 1, wherein said taking into account a geometry of the tomographic imaging comprises characterizing the geometry with a projection matrix.

6. A method according to claim 1, wherein said taking into account a geometry of the tomographic imaging comprises providing an algorithm for computing at least one element of a projection matrix, in which the projection matrix characterizes the geometry.

7. A method according to claim 1, wherein the determined filter component, when used in said analytical tomographic reconstruction technique to reconstruct a first spatial representation of a volume of interest from a projection data set obtained by performing said tomographic imaging, produces a first value in the first spatial representation at said at least one reference location that is substantially equal to a second value in a second spatial representation at said at least one reference location, in which the second spatial representation is obtained by applying said algebraic reconstruction algorithm to the projection data set.

8. A method according to claim 1, wherein the algebraic reconstruction algorithm comprises ART or SIRT.

9. A method according to claim 1, wherein the analytic tomographic reconstruction technique comprises filtered backprojection.

10. An analytic tomographic reconstruction for reconstructing a spatial representation of a volume of interest, comprising the steps of
applying a filter component calculated using a method according to claim 1,
determining projection data by scanning the volume of interest with a tomographic imaging device, the projection data comprising a plurality of projection views obtained from a plurality of projection angles, each projection view comprising a plurality of observation values obtained at a plurality of detection locations, and
reconstructing the spatial representation of the volume of interest using the projection data, the filter component and a backprojection operation.

11. A method according to claim 10, wherein at least one sectional planar representation of the volume of interest is reconstructed.

12. A method according to claim 10, wherein at least one volumetric representation of the volume of interest is reconstructed.

13. A method according to claim 10, wherein the projection data are determined using conical beam geometry.

14. A method according to claim 10, wherein the projection data are determined using fan beam geometry.

15. A method according to claim 10, wherein said reconstructing comprises applying the filter component resulting in a least square approximation resulting in an effective averaging of noise on the projection data.

16. A filter component for an analytical tomographic reconstruction technique used in tomographic imaging, obtained by a method according to claim 1.

17. A non-transitory computer-readable medium having instructions stored therein, which, when implemented on one or more processing units, cause the one or more processing units to perform a method for applying in a tomographic imaging system a filter component for an analytical tomographic reconstruction technique used in tomographic imaging in the tomographic imaging system, the method comprising:
obtaining an algebraic reconstruction algorithm for reconstructing a spatial representation of a volume of interest from a projection data set, the algebraic reconstruction algorithm taking into account a geometry of the tomographic imaging,
applying the algebraic reconstruction algorithm to a plurality of virtual projection data sets to produce a plurality of reconstructed spatial representations, and
determining the filter component using the plurality of reconstructed spatial representations,
implementing the filter component in the tomographic imaging system, wherein each virtual projection data set correspond with a basis vector of a basis for the projection space.

18. A data storage device for storing a filter component according to claim 16.

19. An image or volumetric image obtained by an analytic tomographic reconstruction method for reconstructing a spatial representation of a volume of interest according to claim 10.

* * * * *